US009995735B2

(12) United States Patent
Loneragan et al.

(10) Patent No.: US 9,995,735 B2
(45) Date of Patent: Jun. 12, 2018

(54) **METHOD TO INTRODUCE *SALMONELLA* INTO GROUND MEAT**

(71) Applicants: Texas Tech University System, Lubbock, TX (US); United States Department of Agriculture, College Station, TX (US)

(72) Inventors: Guy Loneragan, Wolfforth, TX (US); Thomas Edrington, College Station, TX (US); Katelyn Malin, Slocomb, AL (US)

(73) Assignee: Texas Tech University System, Lubbock, TX (US)

( * ) Notice: Subject to any disclaimer, the term of this patent is extended or adjusted under 35 U.S.C. 154(b) by 0 days. days.

(21) Appl. No.: 15/261,335

(22) Filed: Sep. 9, 2016

(65) Prior Publication Data

US 2017/0074862 A1 Mar. 16, 2017

Related U.S. Application Data

(60) Provisional application No. 62/216,565, filed on Sep. 10, 2015.

(51) Int. Cl.
| | |
|---|---|
| *A61K 39/108* | (2006.01) |
| *A61K 39/00* | (2006.01) |
| *A61K 39/02* | (2006.01) |
| *G01N 33/50* | (2006.01) |
| *C12Q 1/18* | (2006.01) |
| *A61K 39/112* | (2006.01) |

(52) U.S. Cl.
CPC ..... *G01N 33/5091* (2013.01); *A61K 39/0275* (2013.01); *C12Q 1/18* (2013.01); *G01N 2333/255* (2013.01); *G01N 2800/26* (2013.01); *G01N 2800/52* (2013.01)

(58) Field of Classification Search
CPC ...... A61K 39/00; A61K 39/02; A61K 39/025; A61K 39/0258; A61K 39/0275; A61K 39/0283; A61K 39/0291; A61K 39/07; A61K 39/08; A61K 39/085; A61K 39/092
USPC ......... 424/184.1, 234.1, 243.1, 244.1, 246.1, 424/247.1, 257.1, 258.1
See application file for complete search history.

(56) References Cited

U.S. PATENT DOCUMENTS

| | | | |
|---|---|---|---|
| 4,205,689 | A | 6/1980 | Brennan |
| 4,222,392 | A | 9/1980 | Brennan |
| 5,104,620 | A | 4/1992 | Wiley et al. |

OTHER PUBLICATIONS

Arthur et al., "Prevalence and Characterization of *Salmonella* in Bovine LymphNodes Potentially Destined for Use in Ground Beef." Journal of Food Protection, Mar. 7, 2008, vol. 71, No. 8, pp. 1685-1688.
Bosilevac et al., "Prevalence and Characterization of Salmonellae in Commercial Ground Beef in the United States." Applied and Environmental Microbiology, Apr. 2009, vol. 75, No. 7, pp. 1892-1900.
Brichta-Harhay et al., "Diversity of Multidrug-Resistant *Salmonella enterica* Strains Associated with Cattle at Harvest in the United States." Applied and Environmental Microbiology, Mar. 2011, vol. 77, No. 5, pp. 17831796.
Brichta-Harhay et al., "*Salmonella* and *Escherichia coli* O157:H7 Contamination on Hides and Carcasses of Cull Cattle Presented for Slaughter in the United States: an Evaluation of Prevalence and Bacterial Loads by Immunomagnetic Separation and Direct Plating Methods." Applied and Environmental Microbiology, Oct. 2008, vol. 74, No. 20, pp. 6289-6297.
Brichta-Harhay et al., "Microbiological Analysis of Bovine Lymph Nodes for the Detection of *Salmonella enterica*." Journal of Food Protection, Jan. 14, 2012, vol. 75, No. 5, pp. 854-858.
Edrington et al., "Variation in the faecal shedding of *Salmonella* and *E. coli* O157:H7 in lactating dairy cattle and examination of *Salmonella* genotypes using pulsed-field gel electrophoresis." Letters in Applied Microbiology, Jan. 22, 2004, vol. 38, pp. 366-372.
Edrington et al., "Development of Challenge Models to Evaluate the Efficacy of a Vaccine to Reduce Carriage of *Salmonella* in Peripheral Lymph Nodes of Cattle." Journal of Food Protection, Mar. 4, 2013, vol. 76, No. 7, pp. 1259-1263.
Edrington et al., "Prevalence of Multidrug-Resistant *Salmonella* on Commercial Dairies Utilizing a Single Heifer Raising Facility." Journal of Food Protection, Jan. 2008, vol. 71, No. 1, pp. 27-34.
Edrington et al., "Influence of sprinklers, used to alleviate heat stress, on faecal shedding of *E. coli* O157:H7 and *Salmonella* and antimicrobial susceptibility of *Salmonella* and Enterococcus in lactating dairy cattle." Letters in Applied Microbiology, Jun. 2009, vol. 48, No. 6, pp. 738-743.
Edrington et al., "Development of a Transdermal *Salmonella* Challenge Model in Calves." Journal of Food Protection, Jul. 2013, vol. 76, No. 7, pp. 1255-1258.
Farrow, Lee Russell., "Quantitative Herd-level Evaluation of a Commercially Available Vaccine for Control of *Salmonella* in Dairy Cattle." Ph.D., Texas A&M University, Dec. 2011, pp. 66.
Fedorka-Cray et al., "Survey of *Salmonella* Serotypes in Feedlot Cattle." Journal of Food Protection, May 1998, vol. 61, No. 5, pp. 525-530.
Gragg et al., "Cross-sectional Study Examining *Salmonella enterica* Carriage in Subiliac Lymph Nodes of Cull and Feedlot Cattle at Harvest." Foodborne Pathogens and Disease, Apr. 8, 2013, vol. 10, No. 4, pp. 368-374.

(Continued)

*Primary Examiner* — Rodney P Swartz
(74) *Attorney, Agent, or Firm* — Edwin S. Flores; Daniel J. Chalker; Chalker Flores, LLP

(57) ABSTRACT

The present invention includes a method of introducing a pathogenic infection into one or more peripheral lymph nodes of an animal for testing of meat, comprising: inoculating at one or more peripheral lymph node drainage areas the animal with a known amount of a known pathogen; harvesting one or more peripheral lymph nodes from the animal; grinding meat or meat trimmings and the one or more peripheral lymph nodes into ground meat; and determining a ratio of a number of peripheral lymph nodes infected to the weight of the meat or meat trimmings used to create the ground meat, wherein the infected ground meat can be used to test interventions against the known pathogen in a grinding process.

23 Claims, 6 Drawing Sheets

(56) References Cited

OTHER PUBLICATIONS

Figure 1:
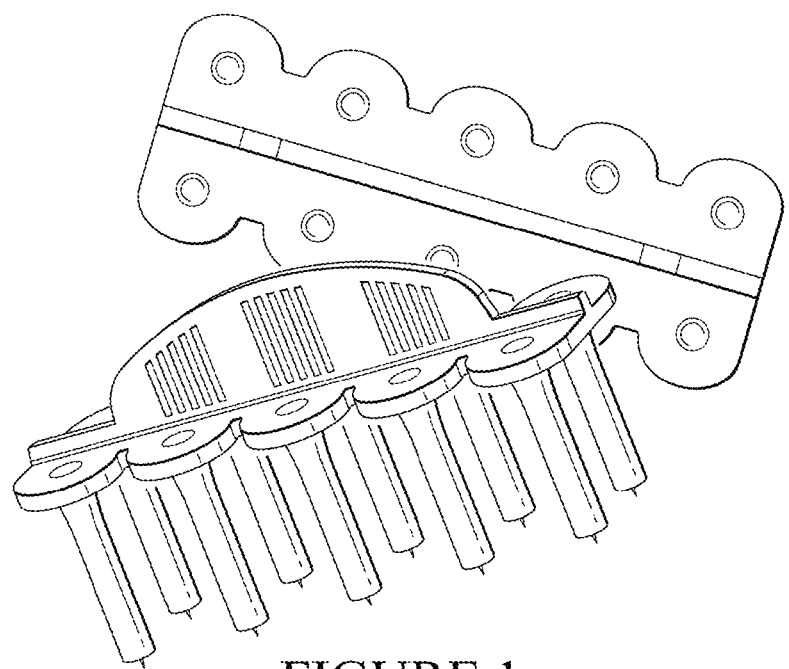
Figure 2:
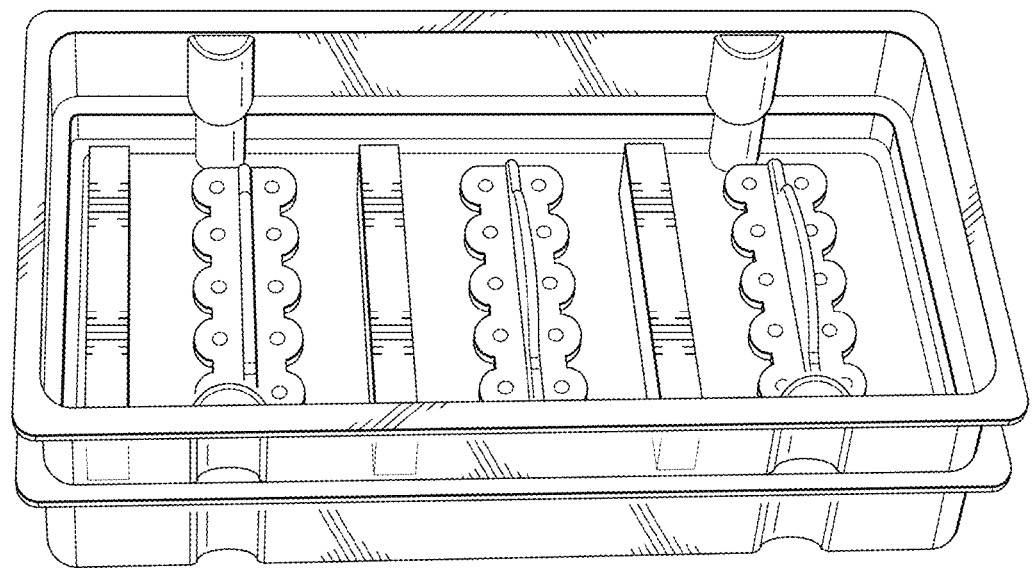
Figure 3:
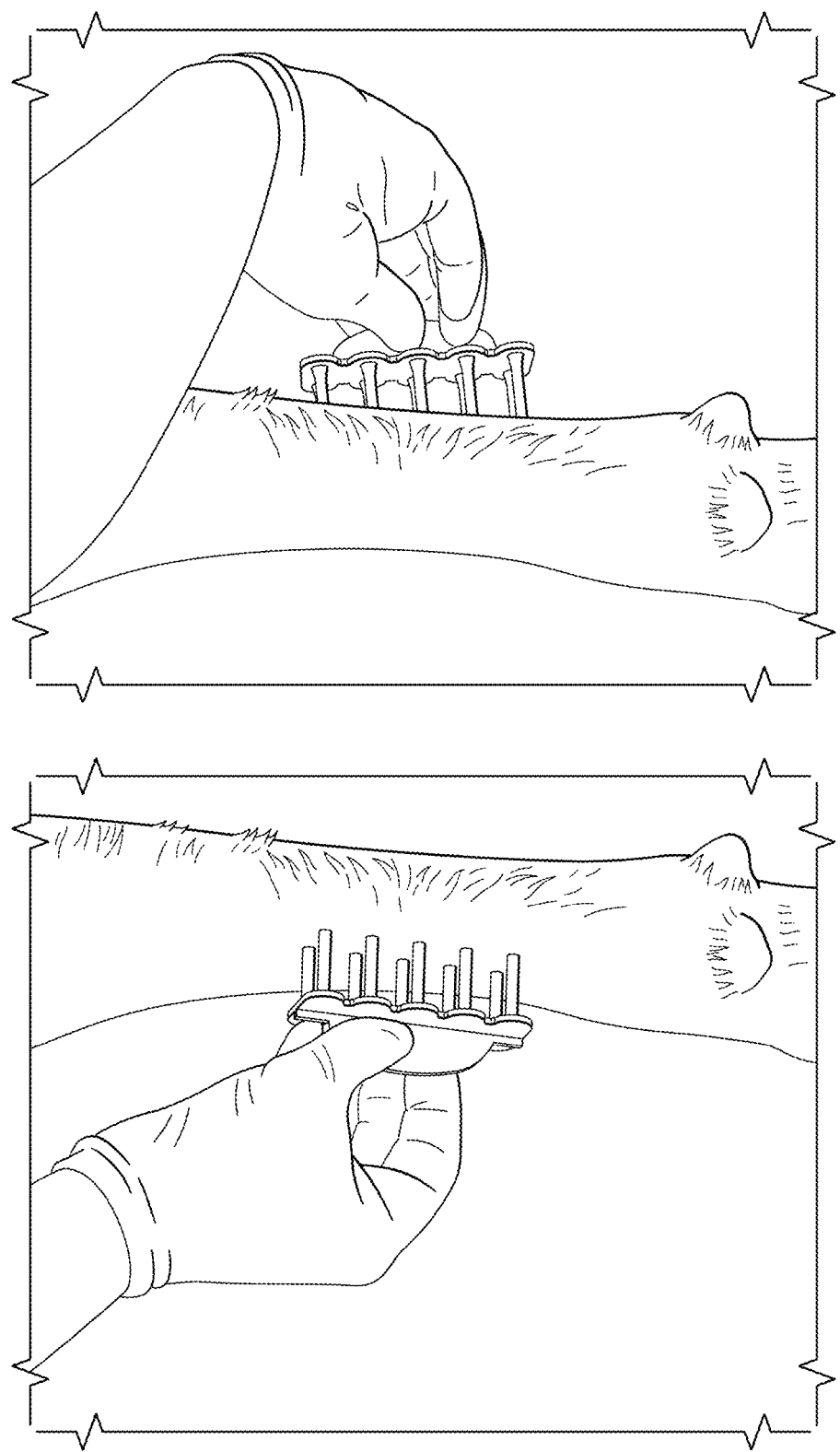

Gragg et al., "Substantial within-Animal Diversity of *Salmonella* Isolates from Lymph Nodes, Feces, and Hides of Cattle at Slaughter." Applied and Environmental Microbiology, Aug. 2013, vol. 79, No. 15, pp. 4744-4750.

Haneklaus et al., "*Salmonella* Prevalence in Bovine Lymph Nodes Differs among Feedyards." Journal of Food Protection, Jun. 2012, vol. 75, No. 6, pp. 1131-1133.

Koohmaraie et al., "Tracking the Sources of *Salmonella* in Ground Beef Produced from Nonfed Cattle." Journal of Food Protection, Aug. 2012, vol. 75, No. 8, pp. 1464-1468.

Kunze et al., "*Salmonella enterica* Burden in Harvest-Ready Cattle Populations from the Southern High Plains of the United States." Applied and Environmental Microbiology, Jan. 2008, vol. 74, No. 2, pp. 345-351.

Loneragan et al., "*Salmonella* Diversity and Burden in Cows on and Culled from Dairy Farms in the Texas High Plains." Foodborne Pathogens and Disease, Jun. 4, 2012, vol. 9, No. 6, pp. 549-555.

Paulin et al., "Analysis of *Salmonella enterica* Serotype-Host Specificity in Calves: Avirulence of *S. enterica* Serotype Gallinarum Correlates with Bacterial Dissemination from Mesenteric Lymph Nodes and Persistence In Vivo." Infection and Immunity, Dec. 2002, vol. 70, No. 12, pp. 6788-6797.

Pullinger et al., "Systemic Translocation of *Salmonella enterica* Serovar Dublin in Cattle Occurs Predominantly via Efferent Lymphatics in a Cell-Free Niche and Requires Type III Secretion System 1 (T3SS-1) but Not T3SS-2." Infection and Immunity, Nov. 2007, vol. 75, No. 11, pp. 5191-5199.

Scallan et al., "Foodborne Illness Acquired in the United States—Major Pathogens." Emerging Infectious Diseases, Jan. 2011, vol. 17, No. 1, pp. 7-15. http://wwwnc.cdc.gov/eid/.

Scharff, L. Robert, "Economic Burden from Health Losses Due to Foodborne Illness in the United States." Journal of Food Protection, Jan. 2012, vol. 75, No. 1, pp. 123-131.

Progress Report on *Salmonella* Testing of Raw Meat and Poultry Products, 1998-2010, US Department of Agriculture 2010 Report, 20 Pages.

METHOD TO INTRODUCE *SALMONELLA* INTO GROUND MEAT

CROSS-REFERENCE TO RELATED APPLICATIONS

This Non-Provisional Patent Application claims priority to U.S. Provisional Patent Application Ser. No. 62/216,565, filed Sep. 10, 2015, the contents of which is incorporated by reference herein in its entirety.

STATEMENT OF FEDERALLY FUNDED RESEARCH

This invention was made with U.S. Government support by the USDA Grant No. 2011-51110-31081. The government has certain rights in this invention.

TECHNICAL FIELD OF THE INVENTION

The present invention relates in general to the fields of immunology and microbiology, and more particularly, to a model for introducing *Salmonella* into ground meat and poultry.

INCORPORATION-BY-REFERENCE OF MATERIALS FILED ON COMPACT DISC

None.

BACKGROUND OF THE INVENTION

Without limiting the scope of the invention, its background is described in connection with inoculation of large animals.

U.S. Pat. No. 4,205,689, issued to Brennan, is directed to an allergy testing system that included a skin testing system for in vivo intracutaneous use that comprises a novel injection unit and multiple applicator, each of the units carrying biological or chemical substances for skin testing, at least one of the units carrying a plurality of different antigens in admixture. Test substances are deposited intracutaneously by piercing the skin with each injection to predetermined depth; and the pierced skin is observed for response to the various substances and dermographia.

U.S. Pat. No. 4,222,392, also issued to Brennan, is directed to an allergy testing device with vented base. The patent is directed to an improved skin test kit comprising a base well and a plurality of injection units held in recessed depressions of the base and removable therefrom. A vent is provided that permits gas to escape during insertion of the injection units. The injection units comprise a hilt portion that may be mated with the periphery of the well depression. A vent hole communicating with a portion of the depression can vent gas through the base bottom, thereby preventing excessive pressure in the well.

U.S. Pat. No. 5,104,620, issued to Wiley, et al., is directed to a disposable allergy skin testing kit. Briefly, a disposable allergy skin testing kit is formed from a top layer sheet, a membrane sheet, and a bottom layer sheet. The bottom sheet has a plurality of recesses formed at predetermined locations to form chambers into which a predetermined antigen has been deposited. The membrane sheet covers these chambers and forms a liquid tight seal and the top layer sheet has an aperture formed in it above each of the antigen chambers. A push button needle assembly is mounted in each of these apertures and it has a disk-shaped pushbutton with a needle extending downwardly from its bottom surface.

SUMMARY OF THE INVENTION

This invention provides a novel method to introduce *Salmonella* into ground meat and poultry through the incorporation of peripheral lymph nodes. Using lymph nodes as a method to introduce an indicator infectious agent or pathogen, e.g., *Salmonella*, to mimic how the indicator infectious agent or pathogen is distributed throughout ground meat during commercial production. The lymph nodes that are incorporated into the ground meat are collected from animals that have been challenged with *Salmonella* via an intradermal, subdermal, or transdermal method. This novel method provides a consistent way to repeatedly recover *Salmonella* from peripheral lymph nodes. This invention further provides a method to develop and test interventions to mitigate *Salmonella* contamination occurring after current post-harvest interventions are applied in abattoirs. Currently, all interventions (other than irradiation, cooking or high pressure) used in commercial abattoirs are applied previous to the product being ground.

In one embodiment, the present invention includes a method of introducing a pathogenic infection into one or more peripheral lymph nodes of an animal for testing of meat, comprising: inoculating at one or more peripheral lymph node drainage areas the animal with a known amount of a known pathogen; harvesting one or more peripheral lymph nodes from the animal; grinding meat or meat trimmings and the one or more peripheral lymph nodes into ground meat; and determining a ratio of a number of peripheral lymph nodes infected to the weight of the meat or meat trimmings used to create the ground meat, wherein the infected ground meat can be used to test interventions against the known pathogen in a grinding process. In one aspect, the inoculation is intradermal, subdermal or transdermal. In another aspect, the pathogen is selected from at least one of *Salmonella, Listeria, Yersinia, Campylobacter, Shigella, E. coli, Francisella, Clostridum, Staphylococcus, Streptococcus*, or *Bacillus*, and strains thereof. In another aspect, the lymph node drainage areas comprise at least one of subiliac, popliteal, retropharangeal, superficial cervical, and axillary. In another aspect, the pathogens are selected from at least one of viral and protozoan pathogens. In another aspect, the animals comprise bovine, equine, ovine, porcine, or caprine. In another aspect, the method further comprises the step of challenging the animal infected with the pathogen at one or more sites with a therapeutic intervention to treat the pathogen. In another aspect, the method further comprises the step of titrating the amount of the known pathogen used during the inoculating step to obtain a pre-determined distribution of infected peripheral lymph nodes. In another aspect, the lymph node drainage areas comprise at least one of subiliac, popliteal, retropharangeal, and superficial cervical. In another aspect, the peripheral lymph nodes do not include gut-associated lymph nodes. In another aspect, the meat is sterile.

In another embodiment, the present invention includes a method of introducing an indicator bacteria into one or more peripheral lymph nodes of an animal comprising: inoculating at one or more sites of the animal a known amount of the indicator bacteria, wherein the one or more inoculation sites comprise one or more peripheral lymph node drainage areas; treating the animal with one or more therapies, treatments, or exposure at one or more time points; harvesting the one or more peripheral lymph nodes from the animal that comprise the inoculated peripheral lymph nodes; grinding the one or more peripheral lymph nodes with a meat or meat trimmings known to be sterile into ground meat; and determining if the one or more therapies, treatments, or exposure were effective to eliminate or reduce the indicator bacteria in the ground meat. In one aspect, the inoculation is intradermal, subdermal or transdermal. In another aspect, the pathogen is selected from *Salmonella, Listeria, Yersinia, Campylobacter, Shigella, E. coli, Francisella, Clostridum, Staphylococcus, Streptococcus*, or *Bacillus*. In another aspect, the lymph node drainage areas comprise at least one of subiliac, popliteal, retropharangeal, superficial cervical, and axillary. In another aspect, the animals comprise bovine, equine, ovine, porcine, or caprine. In another aspect, the method further comprises the step of titrating the amount of the known pathogen used during the inoculating step to obtain a pre-determined distribution of infected peripheral lymph nodes. In another aspect, the lymph node drainage areas comprise at least one of subiliac, popliteal, retropharangeal, and superficial cervical lymph nodes. In another aspect, the peripheral lymph nodes do not include gut-associated lymph nodes.

In yet another embodiment, the present invention includes a method of testing a compound for elimination of bacterial infections within the lymph nodes of an animal comprising: inoculating at one or more sites the animal with a known amount of a bacteria, wherein the one or more inoculation sites comprise peripheral lymph node drainage areas; treating the animal with one or more compounds at one or more time points; harvesting from the animal the inoculated peripheral lymph nodes; grinding the harvested peripheral lymph nodes with meat or meat trimmings that are substantially sterile into ground meat; and determining if the one or more compounds were effective to eliminate or reduce the bacteria. In one aspect, the inoculation is subdermal or transdermal. In another aspect, the bacteria is selected from *Salmonella, Listeria, E. coli, Yersinia, Campylobacter, Shigella, Francisella, Clostridum, Staphylococcus, Streptococcus*, or *Bacillus*. In another aspect, the lymph node drainage areas comprise at least one of subiliac, popliteal, retropharangeal, superficial cervical, and axillary. In another aspect, the animals comprise bovine, equine, ovine, porcine, or caprine. In another aspect, the pathogen is selected from *Salmonella* Newport and Montevideo.

BRIEF DESCRIPTION OF THE DRAWINGS

For a more complete understanding of the features and advantages of the present invention, reference is now made to the detailed description of the invention along with the accompanying figures and in which:

FIG. 1 shows one embodiment of the vaccination device for use with the present invention in which (in this example) 10 inoculation needles are shown;

FIG. 2 shows the loading of vaccine into the inoculation needles;

FIG. 3 shows a trans/intra dermal challenge site for inoculation to the lymph nodes;

FIG. 4 shows the location of the inoculations and the lymph nodes from which the different strains of bacteria were recovered;

FIG. 5 shows the distribution of *Salmonella* in continuous grinds of beef that included 6 nodes per batch. The patterned bars represent positives in sequence (left to right) and solid bars indicate a sample with a quantifiable concentration;

FIG. 6 shows the distribution of *Salmonella* in continuous grinds of beef that incorporated one node per batch of trim. The patterned bars represent positives in sequence (left to right); and FIG. 7 shows the distribution of *Salmonella* concentration in ground beef samples.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Example 1: Development of a Trans- and Intra-Dermal Route of Inoculation

The present inventors developed a trans- and intra-dermal route of inoculation to challenge calves with bacteria such as *Salmonella*. A multi inoculator (e.g., lancet) allergy skin-testing device is inoculated with a *Salmonella* broth and applied with mild pressure to specific regions of the bovine's hide that are drained to region-specific lymph nodes. This process may be repeated at the time of initial inoculation or at subsequent days.

FIG. 1 shows one embodiment of the vaccination device for use with the present invention in which (in this example) 10 inoculation needles are shown. FIG. 2 shows the loading of vaccine into the inoculation needles. FIG. 3 shows a trans/intra dermal challenge site for inoculation to the lymph nodes. FIG. 4 shows the location of the inoculations and the lymph nodes from which the different strains of bacteria were recovered.

At various time-points after inoculation, the cattle are sacrificed and target lymph nodes are aseptically harvested and *Salmonella* is recovered and/or detected by culture and isolation or non-culture based detection assays. The method is applicable to many *Salmonella* serotypes and predictably results in *Salmonella*-positive lymph nodes. Inoculation of the hind leg results in *Salmonella* recovery from the Popliteal lymph node. Inoculation of the ventral abdomen results in *Salmonella* recovery from the Subiliac lymph node. Inoculation of the fore leg results in *Salmonella* recovery from the Prescapular lymph node.

The present inventors recognized that non-mesenteric lymph nodes in cattle may be a significant source of, e.g., *Salmonella, Listeria, E. coli, Yersinia, Campylobacter, Shigella, Francisella, Clostridum, Staphylococcus, Streptococcus*, or *Bacillus* contaminating ground beef. The objective of this work was to determine whether, e.g., a commercially-available *Salmonella* vaccine protects calves from lymph node colonization following significant oral challenge with two strains of *Salmonella* frequently isolated from dairy cattle, *Salmonella* Newport and Montevideo.

Briefly, thirty-two Holstein calves were purchased from a calf ranch in the panhandle of Texas and transported to a laboratory in College Station, Tex. One week following arrival (d 0), all calves were randomly assigned to treatment (Control or Vaccine; n=16 hd/treatment). Vaccinate calves were administered a commercially-available *Salmonella* Newport SRP vaccine (2 ml s.c.) while control calves received a sham-injection of corn oil (2 ml s.c.). A second booster vaccination and sham-injections were administered on d 21. Body weights were recorded weekly throughout the study period and rectal swabs collected at time of weighing on d 0, 7, 14, 21 and 28. On d 33, calves were assigned to pen (8 pens, 4 calves per pen) and inoculated *Salmonella* strain (Montevideo or Newport; 4 pens/strain). On d 35, all calves were inoculated with either *Salmonella* Montevideo or Newport resulting in four treatments: Control—Newport; Control—Montevideo; Vaccine—Newport; Vaccine—Montevideo; eight calves and two pens per treatment. On d 49 (14 d post-inoculation) one-half of the calves (Group 1) in each pen (and treatment) were euthanized and necropsied.

The following lymph nodes were collected and cultured for the challenge strains of *Salmonella*: subiliac (left and right), popliteal (left and right), retropharangeal, superficial cervical (left and right), and mesenteric (ileo-cecal). On d 56 (21 d post-inoculation), all remaining calves (Group 2) were euthanized and necropsied. All lymph nodes were quantitatively and qualitatively cultured for the challenge strains of *Salmonella*. Very few lymph nodes contained quantifiable populations. The percentages of *Salmonella*-positive lymph nodes following enrichment were much higher, although at 14 d post-inoculation (Group 1), no significant treatment differences were observed in the percentage of lymph nodes positive for *Salmonella* Montevideo or Newport. However at 21 d post-inoculation, there were fewer (P<0.05) right popliteal (0 versus 75%) and right pre-scapular nodes (0 versus 75%) that were *Salmonella* positive in the Vaccine—Newport compared to Control—Newport treatments. The percentage of left popliteal and left pre-scapular nodes likewise tended (P=0.10) to decrease in the Vaccine-Newport treatment compared to non-vaccinated controls, while more ileo-cecal lymph nodes tended (P=0.10) to be positive in the Vaccine-Newport treatment. *Salmonella*-positive mandibular nodes tended (P=0.10) to increase in the Vaccine—Montevideo treatment compared to Control—Montevideo calves. All fecal swabs, collected weekly for five weeks prior to *Salmonella* infection, were culture negative. Post-inoculation fecal samples were not affected by treatment (P>0.05) for either strain, although in Group 2 there was a tendency (P=0.09) for the Control-Newport calves to shed lower concentrations of *Salmonella* compared to the Vaccine-Newport animals. Initial and final body weights and overall body weight change were not different (P>0.05) due to treatment. While no treatment effects were observed in the Group 1 calves, the data from Group 2 suggests that the vaccine may have been more effective with additional time between initial infection and necropsy and/or a lower challenge dose of *Salmonella*.

Figure 4:
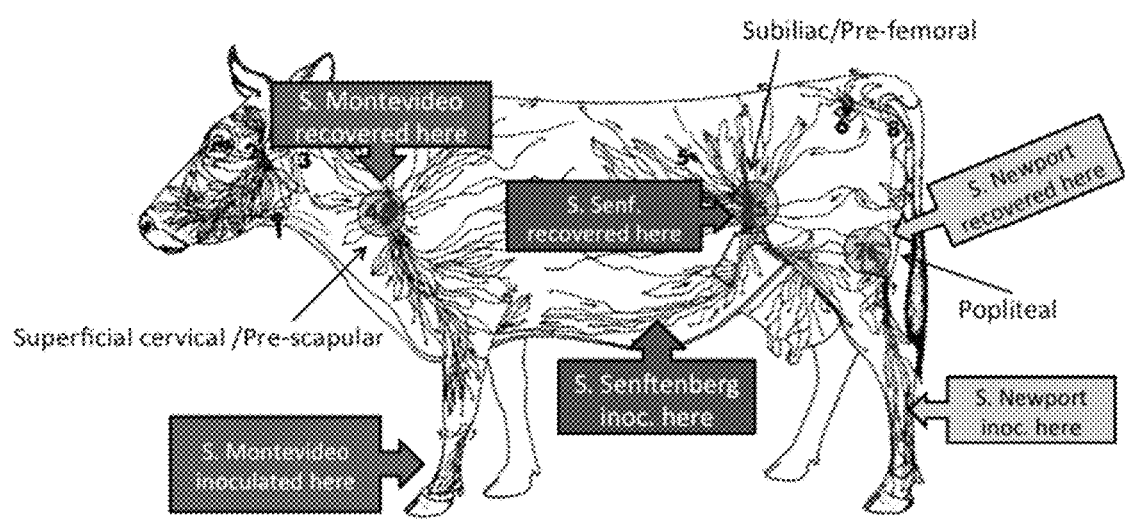

A second study was conducted identical to the above study with the exception that the challenge dose of *Salmonella* was lower ($10^7$ vs $10^8$) and the time frame between challenge and necropsy extended. Lymph nodes collected on 14 and 28 d post-challenge (16 steers) were all culture negative, therefore the study was terminated and future oral challenge models will employ a higher challenge dose and/or multiple challenges. A third pilot study was recently initiated to determine if intra-dermal application of *Salmonella* is capable of infecting non-mesenteric lymph nodes. Early results were positive and the potential model is currently under further investigation. FIG. 4 shows the location of the inoculations and the lymph nodes from which the different strains of bacteria were recovered.

Example 2: Development of a Transdermal *Salmonella* Challenge Model in Calves

Recent investigations have found that *Salmonella* can be routinely recovered from peripheral lymph nodes (PLNs) of cattle presented for harvest. When contained within the PLNs, this foodborne pathogen is protected from currently used postharvest, in-plant intervention strategies and, therefore, PLNs harboring *Salmonella* may be a potential contaminant of ground beef. The objective of this work was to develop a challenge model that effectively and repeatedly results in *Salmonella*-positive PLNs. A 10-lancet skin-allergy instrument was inoculated with *Salmonella*, and calves were inoculated intra- and/or transdermally by applying the device over various ventral regions of the skin. *Salmonella* was successfully and predictably recovered from region-specific PLNs up to 8 days postchallenge. Furthermore, serotypes inoculated within specific regions were only recovered from the PLNs draining those regions. This model provides a method to predictably infect PLNs with *Salmonella*. Further, this model makes it possible to determine the duration of infection and to evaluate candidate interventions that may shorten the duration of infection.

Recent reports indicate that it is not uncommon to recover *Salmonella* from the peripheral lymph nodes (PLNs) of cattle presented for harvest (1, 6); moreover, others have implicated *Salmonella*-positive PLNs as a likely source of *Salmonella* in ground beef (7). Because *Salmonella* is a gastrointestinal pathogen (2-4), it seems logical that PLN infection by *Salmonella* occurs via systemic spread from the gastrointestinal tract. This hypothesized route has been supported by studies in which *Salmonella* was isolated from the mesenteric lymph nodes of healthy cattle at slaughter (10) and systemic translocation of *Salmonella* from the small intestine was found to occur via the lymphatic system (8, 9). However, recent attempts in the inventors' laboratory to develop a model of *Salmonella* infection of the PLNs using an oral challenge (5) have produced inconsistent and, therefore, unpredictable results.

It is possible that *Salmonella* may infect PLNs, whereby *Salmonella* crosses the host's integument transdermally. This may occur as a consequence of abrasions, diseases of the integument, or other means such as biting flies, whereby *Salmonella* is introduced intradermally or transdermally and then transported from the interstitial spaces to the regional draining PLNs. The present invention includes a model in which *Salmonella* is challenged either intradermally or transdermally may provide a more consistent infection of PLNs. The objective of this study was to develop and evaluate the intra- and transdermal routes of inoculation as potential models of PLN infection with *Salmonella*.

Materials And Methods. Care, use, and handling of experimental animals were preapproved by the Animal Care and Use Committee of the Food and Feed Safety Research Laboratory, U.S. Department of Agriculture. Because of the unknowns associated with a transdermal route of inoculation and because these studies were necessarily terminal in nature, a series of studies were developed to provide proof of principle and subsequent model development while limiting the number of animals involved. All steers were individually penned in covered, concrete floored pens with feed (hay and grain) and ad libitum water to meet the animal's nutritional requirements.

Study I. Of five Holstein steers (approximate body weight 635 kg), three were inoculated with Salmonella and two were controls. Animals were restrained in a squeeze chute, and each leg was immobilized. Salmonella inocula were injected intradermally above the metacarpus and metatarsus using a 1.0-ml tuberculin syringe fitted with a 22-gauge, 1.5-in. needle. Tryptic soy broth (TSB, 1 ml) containing the Salmonella ($10^8$ CFU Salmonella per ml) or corn oil (control) was administered in a series of five injections (0.2 ml per injection site) in each of the four legs. Four serovars were used: pansusceptible Salmonella Montevideo was inoculated in the right foreleg, multidrug-resistant (MDR) Salmonella Newport in the left foreleg, MDR Salmonella Typhimurium in the right rear leg, and pansusceptible Salmonella Senftenberg in the left rear leg. Steers were necropsied 2, 3, and 4 days following treatment administration (one treated steer on day 2; one control and one treated steer on each of days 3 and 4). Steers were euthanized (Euthasol, Delmarva Laboratories, Inc., Midlothian, Va.), and the right and left subiliacs, popliteal, and superficial cervical nodes were collected, weighed, and cultured for the challenge strains of Salmonella.

Study II. One Holstein steer (approximate body weight 150 kg) was utilized to evaluate an alternative method for intradermal inoculation of Salmonella. A 10-microlancet, skin allergy testing instrument (ComforTen Multiple Skin Test Device, Hollister-Stier Allergy, Spokane, Wash.) was dip inoculated with MDR Salmonella Typhimurium (TSB with $4.5 | 10^8$/ml Salmonella) or pansusceptible Salmonella Senftenberg (TSB with $3.8 | 10^8$/ml Salmonella). The instrument is designed to penetrate intradermally, not subcutaneously. The inoculated instrument was applied with light pressure both medially and laterally (twice each) above the metacarpus and metatarsus of the steer; Salmonella Typhimurium was inoculated in the right legs and Salmonella Senftenberg in the left legs. In between applications (i.e., four applications per leg), the 10-lancet instrument was redipped into the appropriate Salmonella broth, and a new instrument was used for each leg. Two days following Salmonella challenge, the steer was euthanized and necropsied as above and Salmonella was cultured.

Study III. Two Holstein steers (approximate body weight 180 kg) were used to further examine the suitability of the 10-lancet inoculation instrument. Each steer was challenged with MDR Salmonella Newport (instrument was dip inoculated into TSB with 1.9 to $3.7 | 10^8$ Salmonella per ml) administered to each leg (five instrument applications per leg; one anterior and two each on medial and lateral sides of metacarpus and metatarsus). Each leg was inoculated at different times, with the right fore, right rear, left fore, and left rear legs inoculated 2, 4, 6, and 8 days prior to necropsy, respectively. Steers were euthanized and lymph nodes harvested as described above.

Lymph node processing and bacterial culture. Lymph nodes were transferred to the laboratory within 30 min of collection and processed as described previously (1). Tetrathionate broth (20 ml) was added to each sample bag containing the processed lymph node and was mixed for 60 s. For quantitative estimation, 1 ml of the pulverized lymph node-tetrathionate broth mixture was removed and 50 ml was direct plated on xylose lysine deoxycholate agar using a commercially available spiral plater (Spiral Biotech Autoplate 4000, Advanced Instruments, Inc., Norwood, Mass.). Plates were incubated (37° C., 24 h), followed by an additional 24 h at room temperature. Black colonies were counted and converted to log CFU per gram lymph node tissue. Following spiral plating, an additional 80 ml of tetrathionate broth was added and the lymph node-tetrathionate mixture was incubated overnight (37° C.). Then 100 ml of the enrichment was transferred to 5 ml of Rappaport-Vassiliadis broth and incubated at 42° C. for 24 h, prior to plating on brilliant green agar supplemented with novobiocin (25 mg/ml). Plates were incubated (37° C., overnight), and presumptive Salmonella isolates were serogrouped (five isolates per positive sample) using slide agglutination with Salmonella antiserum (Difco Laboratories, Detroit, Mich.).

Results. The intradermal route of inoculation described herein predictably resulted in Salmonella-positive PLNs. In the first study, the majority of PLNs examined in the three Salmonella-treated steers were culture positive for the specific challenge strains, and most contained significant quantifiable concentrations (2.9 to 5.3 log CFU/g lymph node tissue; Table 1). The exceptions were that all subiliac lymph nodes were culture negative. Furthermore, the route of inoculation provided excellent serotype-region specificity;

TABLE 1

Concentration, prevalence (positive or negative), and serogroups of Salmonella isolates recovered from the peripheral lymph nodes of three steers inoculated intradermally in the lower legs with four different Salmonella serotypes (proof of principle study I)

| Leg | Inoculated serogroup | Lymph node | Steer No. 8 CFU/g | ± | Steer No. 20 CFU/g | ± | Steer No. 22 CFU/g | ± |
|---|---|---|---|---|---|---|---|---|
| Right fore | $C_1$ | Superficial Cervical | 3.4 | Pos | 5.2 | Pos | 4.6 | Pos |
| Right hind | B | Popliteal | 2/2 $C_1$ 4.2 | 5/5 $C_1$ Pos | 5/5 $C_1$ 5.3 | 5/5 $C_1$ Pos | 5/5 $C_1$ 4.7 | 5/5 $C_1$ Pos |
| Left fore | $C_2$ | Subiliac | 5/5 B Neg | 5/5 B Neg | 5/5 B Neg | 5/5 B Neg | 5/5 B Neg | 5/5 B Neg |
| | | Superficial cervical | 3.6 | Pos | 4.4 | Pos | 4.5 | Pos |
| Left hind | $E_4$ | Popliteal | 3/3 $C_2$ Neg | 5/5 $C_2$ Pos | 5/5 $C_2$ 2.9 | 5/5 $C_2$ Pos | 5/5 $C_2$ 3.7 | 5/5 $C_2$ Pos |
| | | Subiliac | Neg Neg | 5/5 $E_4$ Neg | 1/1 $E_4$ Neg | 5/5 $E_4$ Neg | 5/5 $E_4$ Neg | 5/5 $E_4$ Neg | the inventors only recovered the serotype (represented by distinct serogroups) from the PLNs that drain the region of inoculation. We did not recover any *Salmonella* from the PLNs of the two control steers. Mild to moderate swelling and lameness were observed in the steers inoculated with *Salmonella* but not in the controls. Although every effort was made to administer the *Salmonella* intradermally, controlling the depth of the injection using the tuberculin syringe was difficult.

Because of the challenge using the syringe and lameness issues, the inventors then used the 10-microlancet instrument. No swelling or lameness was observed following the use of this instrument; furthermore, it required minimal animal restraint and improved the ease of application. Use of this instrument in the second proof of principle study resulted in recovery of *Salmonella* from both the left popliteal and left superficial cervical PLNs, whereas those of the right legs and the subiliac nodes were culture negative (data not shown). In contrast to the first study, however, the concentration of *Salmonella* within the PLNs was below the limit of quantification. Isolates cultured from the lymph nodes of the left leg all belonged to serogroup B, the same serogroup administered to the left legs. Results from the third proof of principle study were similar to the second. In one steer, *Salmonella* was recovered from both right and left superficial cervical and popliteal PLNs; in the other steer, *Salmonella* was only recovered from the left superficial cervical PLNs (Table 2). None of the PLNs contained quantifiable *Salmonella* populations. All lymph node isolates belonged to serogroup C2, the same serogroup used to inoculate all legs in both animals. *Salmonella* was recovered from the lymph nodes at 2, 4, 6, and 8 days postinoculation. All subiliac lymph nodes were culture negative.

of inoculation predictably results in *Salmonella*-positive PLNs for at least 8 days postinoculation. With this approach, an estimate of the duration of infection can be made, and the impact of interventions, such as a vaccine, on the duration of infection can be evaluated. Duration of infection is an important biological attribute because prevalence, e.g., prevalence of *Salmonella*-positive PLNs in cattle presented for harvest, is a function of incidence and duration of infection. Incidence, rate of new PLN infections per unit time, is difficult to measure directly in real-world settings, but it can be estimated if the duration of infection is known. A further advantage is that this model allows examination of the effect of an intervention against multiple serotypes within an individual animal and the individual can serve as its own control, given the regional specificity of inoculation and recovery. This salient observation will reduce the number of animals required in future challenge models.

The 10-microlancet instrument is that a single-day inoculation resulted in concentrations of *Salmonella* within PLNs that were below the limit of quantification, yet this approach did not result in lameness or swelling and was well tolerated by the animals. On the other hand, the syringe application provided predictably quantifiable concentrations of *Salmonella* in the regional PLNs, but unfortunately, this method of inoculation (and the amount of inoculum) resulted in overt lameness and swelling and was difficult to administer. A further limitation of the approaches described herein is that none of the subiliac PLNs were positive for *Salmonella* following inoculation. This may be viewed as an important shortcoming since most of the work demonstrating recovery of *Salmonella* from PLNs of cattle presented for harvest has used the subiliac PLNs. In a companion paper (5), however, the inventors describe the use of a 10-microlancet instrument to inoculate *Salmonella* intradermally over the ventral abdomen region, resulting in predictably positive subiliac PLNs.

TABLE 2

*Salmonella* recovery (concentration, prevalence [positive or negative], and isolate serogroup) from the peripheral lymph nodes in steers receiving intradermal administration of *Salmonella* in the lower legs and necropsied 2, 4, 6, or 8 days postinoculation (proof of principle study III)

| | | | | Steer | | | |
|---|---|---|---|---|---|---|---|
| | Inoculated | Days | | No. 33 | | No. 35 | |
| Leg | serogroup | Postomoculation | Lymph node | Concn | ± | Concn | ± |
| Right fore | $C_2$ | 2 | Superficial cervical | Neg | Pos 5/5 $C_2$ | Neg | Neg |
| Right hind | $C_2$ | 4 | Popliteal | Neg | Pos 5/5 $C_2$ | Neg | Neg |
| | | | Subiliac | Neg | Neg | Neg | Neg |
| Left fore | $C_2$ | 6 | Superficial cervical | Neg | Pos 5/5 $C_2$ | Neg | Pos 5/5 $C_2$ |
| Left hind | $C_2$ | 8 | Popliteal | Neg | Pos 5/5 $C_2$ | Neg | Neg |
| | | | Subiliac | Neg | Neg | Neg | Neg |

The present inventors describe the development of a challenge model that predictably results in *Salmonella*-positive PLNs. The intradermal route of inoculation is novel and somewhat unconventional, but the inventors believe it is an appropriate approach to determine that a proportion of the *Salmonella* observed in PLNs of cattle presented for harvest in the United States crosses the integument transdermally. This model provides distinct advantages over other routes of infection used, such as oral or intravenous. First, this route The studies described demonstrate the use of the present invention despite the number of animals in each study. Animals of different sizes were used. Despite the number of animals and the various sizes, the intradermal route of inoculation proved to be predictable and a suitable challenge model to result in *Salmonella*-positive PLNs. However, the excellent specificity of the serogroups recovered to those of the regionally inoculated strains suggests that prior exposure is not a high probability.

Example 3: Development of Challenge Models to Evaluate the Efficacy of a Vaccine to Reduce Carriage of *Salmonella* in Peripheral Lymph Nodes of Cattle Because challenge models to infect peripheral lymph nodes (PLNs) with *Salmonella* have not been reported, the inventors performed a series of studies to develop and refine challenge models to evaluate an intervention applied at the animal level and to provide initial estimates of efficacy of an intervention (i.e., a vaccine) to aid in the design of future studies. In each of four studies, steers (control or vaccinated) were inoculated with *Salmonella* strains Montevideo or Newport, and in study IV, *Salmonella* Senftenberg was also used. Calves were euthanized 14 to 42 days postinoculation, and PLNs were collected. In the first study, calves were challenged with, $10^{10}$ *Salmonella* cells, and few treatment differences were observed 14 days postchallenge. However, by day 21, *Salmonella* Newport was recovered from fewer vaccinated calves than control calves ($P<0.05$). In study II, calves were challenged with, $10^{7}$ *Salmonella* cells and, after two necropsies (14 and 28 days postchallenge), only one lymph node was *Salmonella* positive; therefore, the study was terminated. In study III, calves were again challenged with, $10^{10}$ *Salmonella* cells, and no significant effect of vaccine was observed in calves challenged with Montevideo or Newport strains. A transdermal route of challenge was explored in study IV, using a 10-lancet, allergy testing instrument. Sixteen steers were challenged with either *Salmonella* Newport or *Salmonella* Montevideo (*Salmonella* Newport right legs; *Salmonella* Montevideo left legs), and all steers were challenged on the lower abdomen with *Salmonella* Senftenberg. Transdermal inoculation resulted in predictably *Salmonella*-positive PLNs, and a modest vaccine effect was detected. Because it is well tolerated by the calves and results in predictable and regionally specific *Salmonella* recovery from PLNs, the transdermal route of challenge may be preferred by researchers wishing to evaluate the impact of interventions designed to reduce the carriage of *Salmonella* in PLNs.

Recent research suggests that *Salmonella* may be commonly harbored in peripheral lymph nodes (PLNs) of cattle presented for harvest (1, 7, 10). Because PLNs are frequently included in ground beef, *Salmonella* carriage in PLNs likely results in some degree of *Salmonella* contamination of ground beef. It may be practical to remove large, easily accessible PLNs during harvest; however, it is impractical to remove all PLNs, as cattle have many small PLNs throughout their carcasses. It is possible that preharvest control of *Salmonella* may complement within-plant control efforts and reduce the likelihood of ground beef contamination. A vaccine containing siderophore receptors and porin proteins from *Salmonella* Newport was associated with reduced shedding of *Salmonella* in the feces of dairy cattle (6, 11). In another study (9) of this vaccine, no difference in fecal *Salmonella* prevalence was observed, although the *Salmonella* prevalence and study design did not lend itself to such a comparison. No differences were observed in fecal shedding of *Salmonella* in studies of feedlot cattle (2) or dairy cows (8). It is possible, however, that immunity against *Salmonella* may reduce the duration of infection within lymph nodes regardless of an effect, or lack thereof, within the lumen of the intestine. If so, this vaccine may reduce the prevalence of *Salmonella* within the PLNs of cattle presented for harvest.

Because challenge models to infect PLNs with *Salmonella* have not been reported, the inventors performed a series of four studies to develop and refine challenge models that can be used to evaluate an intervention applied at the animal level and to provide initial estimates of efficacy of an intervention (i.e., a vaccine) that can be used by researchers to aid the design of future studies.

Materials And Methods. Care, use, and handling of experimental animals were preapproved by the Animal Care and Use Committee of the Food and Feed Safety Research Laboratory, U.S. Department of Agriculture. Recently weaned Holstein and Holstein-cross steers were purchased from a single supplier and transported to the laboratory in College Station, Tex. Upon arrival, steers were weighed, identified with an ear tag, and maintained in a large outside lot and fed a commercial nonmedicated calf starter and grass hay. In study I, symptoms of bovine respiratory disease were observed in most steers, and all were administered enrofloxacin (Baytril 100, Bayer Animal Health LLC, Shawnee Mission, KS). In subsequent studies, steers were metaphylactically administered tulathromycin (Draxxin, Pfizer Animal Health, New York, N.Y.) per manufacturer's recommendations upon arrival. Rectal swabs were collected weekly prechallenge and were cultured for *Salmonella*. Following acclimation (3 to 5 weeks), steers were randomly assigned to treatment (control or vaccine). Vaccinated steers were administered a commercially available *Salmonella* vaccine on days 0 and 21 per label directions (2 ml subcutaneous; *Salmonella* Newport Bacterial Extract vaccine with SRP Technology, Pfizer Animal Health, Madison, N.J.), whereas control animals received a sham injection of corn oil (2 ml subcutaneous). Steers were housed outdoors in covered, concrete floored pens, either two or four steers per pen, and were fed a diet to meet or exceed their nutritional requirements. Pens were washed daily. Steers were euthanized (Euthasol, Delmarva Laboratories, Midlothian, Va.), and the right and left subiliacs, popliteals, and superficial cervical nodes were collected, weighed, and cultured for the challenge strains of *Salmonella* as described below.

Study I. Thirty-two steers (average body weight 81 kg) were inoculated with either *Salmonella* Montevideo or *Salmonella* Newport in a 2|2 factorial design such that there were eight calves per treatment. Calves were challenged orally with 20 ml of tryptic soy broth (TSB) containing 1.0 and 1.2|$10^{10}$ CFU of *Salmonella* Montevideo or *Salmonella* Newport, respectively. Body weights were collected weekly throughout the study period. Fourteen days postchallenge, one-half of the calves in each pen (and treatment) were euthanized and PLNs were collected. At 21 days postchallenge, all remaining calves were euthanized and PLNs were collected.

Study II. The design was similar to that of study I, except that the oral challenge included 4.2 and 6.0|107 CFU of *Salmonella* Montevideo and *Salmonella* Newport, respectively. Two calves per treatment were necropsied 14 and 28 days postchallenge. Due to the poor recovery of *Salmonella* from the PLNs, the study was terminated.

Study III. Using a design similar to that of studies I and II, calves were challenged with 1.5 and 1.3|$10^{10}$ CFU of *Salmonella* Montevideo and *Salmonella* Newport, respectively, in 20 ml of TSB, and two calves per treatment were necropsied on days 14, 28, 35, and 42 postchallenge. In addition to the nodes described above, axillary lymph nodes (right and left) were collected.

Study IV. Sixteen steers (average body weight 193 kg; two per pen by treatment) were randomly allocated to vaccine or control treatment. Calves were challenged with either *Salmonella* Newport (7.9|10$^8$/ml; eight steers) or *Salmonella* Montevideo (1.2|10$^9$/ml; eight steers) using a 10-lancet allergy testing instrument (ComforTen Multiple Skin Test Device, Hollister-Stier Allergy, Spokane, Wash.) as described elsewhere (5). Four applications of this 10-lancet instrument were made to each leg; two applications were medial and two were lateral to the metacarpus-metatarsus, such that *Salmonella* Newport was challenged in the right legs and *Salmonella* Montevideo in the left legs. Additionally, all calves were challenged on the lower abdomen with *Salmonella* Senftenberg (4.3|10$^8$/ml) via two applications each on the right and left sides. A new instrument was used for the different serovars and for each calf. Three and 6 days following *Salmonella* challenge, one-half of the calves in each treatment were euthanized and PLNs were collected.

Lymph node processing. Within 15 min of collection, lymph nodes were transferred to the laboratory and each node was trimmed of excess fat and fascia. Trimmed lymph nodes were weighed and then surface sterilized by immersion in boiling water for 3 s. The sterilized lymph node was placed into a filtered stomacher bag, and the tissue was pulverized using a rubber mallet. Tetrathionate broth (20 ml) was added to each sample bag, followed by mixing for 60 s with a laboratory blender. For quantitative culture, 1 ml of the pulverized lymph node-tetrathionate broth mixture was removed and 50 ml was direct plated on xylose lysine deoxycholate agar using a commercially available spiral plater (Spiral Biotech Autoplate 4000, Advanced Instruments, Inc., Norwood, Mass.). Plates were incubated (37° C., 24 h) followed by an additional 24 h at room temperature. Black colonies were counted and converted to log CFU per gram PLN. Following spiral plating, an additional 80 ml of tetrathionate broth was added, and the lymph node-tetrathionate mixture was incubated overnight (37° C.). A sample (100 ml) of this enrichment was transferred to 5 ml of Rappaport-Vassiliadis broth and incubated at 42° C. for 24 h, and then it was plated for isolation on brilliant green agar supplemented with novobiocin (25 mg/ml). Plates were incubated at 37° C. overnight, and *Salmonella* isolates were serogrouped (three isolates per PLN). Serogrouping was conducted using slide agglutination with *Salmonella* antiserum (Difco, BD, Detroit, Mich.). Rectal swabs were enriched in 20 ml of tetrathionate broth and were incubated at 37° C. overnight; next, 100 ml was inoculated into 5 ml of Rappaport-Vassiliadis broth, incubated as above, and then plated for isolation on brilliant green agar supplemented with novobiocin and incubated as described. Statistical analysis. Data were analyzed using SAS software (version 9.3, SAS Institute Inc., Cary, N.C.). Contingency tables were developed and within-table dependency was evaluated using either a chi-square statistic or a Fisher's exact test. Logistic regression models were constructed to compare treatment effects.

Results. Rectal swabs collected prechallenge were all *Salmonella* negative except for study III, in which a few swabs were positive and all of the isolates belonged to serogroups different from the challenge strains. In study I, *Salmonella* was recovered from 58.3 and 87.5% of PLNs and calves, respectively. No significant differences were observed in the percentage of PLNs positive for *Salmonella* Montevideo or *Salmonella* Newport on day 14 (Table 3). At 21 days postinoculation, *Salmonella* Newport was recovered from fewer ($P<0.05$) PLNs among the vaccinated calves (4%) compared with the control calves (54%). With two exceptions, all recovered isolate serogroups matched the respective challenge strains. Two steers in the Montevideo (serogroup C1) treatment (one each control and vaccine) also had serogroup C2 isolates cultured from their lymph nodes.

TABLE 3

Prevalence of *Salmonella* serovars (Montevideo and Newport) in the peripheral lymph nodes of vaccinated or control calves necropsied 14 or 21 days postchallenge (Study I)[a]

| Lymph node | 14 days postchallenge (n = 16) | | | | 21 days postchallenge (n = 16) | | | |
|---|---|---|---|---|---|---|---|---|
| | Montevideo | | Newport | | Montevideo | | Newport | |
| | Control | Vaccine | Control | Vaccine | Control | Vaccine | Control | Vaccine |
| Subiliac | | | | | | | | |
| Right | 50 | 75 | 50$_A$ | 100$_B$ | 100 | 75 | 25 | 0 |
| Left | 50 | 75 | 75 | 100 | 100 | 75 | 50 | 25 |
| Popliteal | | | | | | | | |
| Right | 50 | 75 | 50 | 50 | 25 | 75 | 75$_C$ | 0$_D$ |
| Left | 50 | 50 | 50$_A$ | 100$_B$ | 100 | 75 | 50$_A$ | 0$_B$ |
| Superficial cervical | | | | | | | | |
| Right | 50 | 75 | 50$_A$ | 100$_B$ | 75 | 75 | 75$_C$ | 0$_D$ |
| Left | 50 | 50 | 50 | 50 | 50$_C$ | 100$_D$ | 50$_A$ | 0$_B$ |
| All nodes | 50 | 67 | 54$_A$ | 83$_B$ | 75 | 79 | 54$_C$ | 4$_D$ |

[a]Vaccine, administered a commercially available *Salmonella* vaccine; Control, administered a sham injection. Values followed by letters A and B indicate that row percentages within necropsy and *Salmonella* strain tend to differ ($P < 0.10$); values followed by letters C and D indicate that row percentages within necropsy and *Salmonella* strain are different ($P < 0.05$).

In study II, *Salmonella* was only recovered from two PLNs harvested during the first two necropsies (14 and 28 days postinoculation); therefore, the study was terminated. The higher challenge dose (i.e., 10$^{10}$) in study III resulted in the recovery of *Salmonella* from PLNs. *Salmonella* was recovered from 35.2 and 62.5% of PLNs and calves, respectively. No significant treatment differences were observed, with one exception: the vaccine treatment decreased ($P<0.05$) the percentage of *Salmonella*-positive left axillary nodes compared with controls across serotypes. *Salmonella* was recovered from fewer PLNs of calves challenged with *Salmonella* Newport than from those challenged with *Salmonella* Montevideo (Table 4). The majority of isolates (98%) matched the serogroup of the challenge strain. The only exceptions were that *Salmonella* Montevideo was cultured from the popliteal and subiliac in one calf on day 35 and from the subiliac in another calf on day 42; both of these calves were inoculated with *Salmonella* Newport. In the transdermal challenge model (study IV), *Salmonella* was recovered from 58.3 and 93.8% of PLNs and calves, respectively. No treatment differences were observed among calves inoculated with *Salmonella* Montevideo, except that there was reduced (P<0.05) likelihood of recovery from the right subiliac lymph nodes among vaccinates compared with controls (Table 5). Across all nodes, the likelihood of recovery of *Salmonella* Newport from PLNs was lower (P=0.03) among vaccinated calves (33.3%) compared with controls (66.7%). All but one isolate matched the serogroup of regional challenge. The only exception was that one isolate from a subiliac lymph node was serogroup C2 (presumably Newport) instead of E4 (i.e., Senftenberg).

TABLE 4

Prevalence of *Salmonella* (Montevideo and Newport) in the peripheral lymph nodes of vaccinated or control calves (Study III)[a]

| Lymph node | Montevideo | | Newport | |
| --- | --- | --- | --- | --- |
| | Control | Vaccine | Control | Vaccine |
| Subiliac | | | | |
| Right | 75 | 87.5 | 25 | 0 |
| Left | 75 | 62.5 | 25 | 12.5 |
| Popliteal | | | | |
| Right | 50 | 62.5 | 12.5 | 12.5 |
| Left | 37.5 | 62.5 | 0 | 12.5 |
| Superficial cervical | | | | |
| Right | 50 | 75 | 0 | 0 |
| Left | 50 | 75 | 0 | 0 |
| Axillary | | | | |
| Right | 50 | 62.5 | 0 | 0 |
| Left | 87.5 | 50 | 0 | 0 |
| All nodes | 56.3 | 70.8 | 10.4 | 6.3 |

[a]Vaccine, administered a commercially available *Salmonella* vaccine; Control, administered a sham injection.

DISCUSSION In the work described herein, the inventors developed two distinct routes of *Salmonella* challenge that resulted in *Salmonella* recovery from PLNs. Because prevalence of *Salmonella* in PLNs is a function of incidence (i.e., rate of new PLN infections) and duration of infection, the inventors included various windows of harvest to capture a change in the duration of infection, given that the inventors attempted to control the incidence (i.e., by providing the challenge at one time point). In study I, the oral challenge, no evidence of a reduction in prevalence was observed 14 days after challenge. After 21 days, a decrease was observed in calves challenged with *Salmonella* Newport, which likely indicated an increased rate of clearance (or reduced duration of infection). Also, a treatment effect was observed in study IV (transdermal), and a numerical reduction was observed in study III. Despite this evidence supporting its efficacy against *Salmonella* Newport, no association (even with a liberal interpretation of P values) was observed for *Salmonella* Montevideo. This may be because there is a lack of antigenic homology between the challenge serotypes or because Montevideo has additional mechanisms for iron acquisition, or it may be due to other variations among host-bacteria interactions.

TABLE 5

Prevalence of *Salmonella*-positive lymph nodes in vaccinated or control calves following transdermal challenge of *Salmonella* to the lower legs and ventral abdomen (Study IV)[a]

| | Montevideo/ Senftenberg | | Newport/ Senftenberg | | Combined Stains | |
| --- | --- | --- | --- | --- | --- | --- |
| Node | Control | Vaccine | Control | Vaccine | Control | Vaccine |
| Subiliac | | | | | | |
| Right | 75$_A$ | 0$_B$ | 25 | 25 | 50 | 12.5 |
| Left | 0 | 25 | 75 | 25 | 38 | 25 |
| Popliteal | | | | | | |
| Right | 75 | 100 | 75 | 50 | 75 | 75 |
| Left | 75 | 75 | 50 | 25 | 63 | 50 |
| Superficial cervical | | | | | | |
| Right | 75 | 100 | 75 | 75 | 75 | 88 |
| Left | 100 | 100 | 100$_A$ | 0$_B$ | 100$_A$ | 50$_B$ |
| All nodes | 67 | 67 | 67$_C$ | 33$_D$ | 67 | 50 |

[a]*Salmonella* strains Montevideo and Newport (n ~16 calves each) were administered to the lower legs; *Salmonella* Senftenberg (all calves) was administered to the ventral abdomen. Vaccine, administered a commercially available *Salmonella* vaccine; Control, administered a sham injection. Values followed by letters A and B indicate that row percentages within *Salmonella* strain are different (P < 0.05); values followed by letters C and D indicate that row percentages within *Salmonella* strain tend to differ (P ≤ 0.10). It is clear from the work described herein that a substantial oral dose (i.e., $10^{10}$) of *Salmonella* is required to result in recovery of *Salmonella* from PLNs. In study II, the lower dose failed to produce *Salmonella* in PLNs at detectable concentrations. On occasion, the inventors did recover serogroups other than the challenge serogroup. It may be that repeated lower doses would have been equally effective as (or even more effective than) a single large challenge. Whereas repeated exposures may better mimic real-world events, the inventors attempted to control incidence to the extent possible so that observed differences in vaccine status (or in serotype status) were primarily a reflection of changes in duration of infection. Once duration of infection is known for specific serotypes, variation in challenge regimens might be explored.

The recovery of serogroup C2 in calves challenged with *Salmonella* Montevideo (i.e., C1) (study I) and of C1 in calves challenged with *Salmonella* Newport (study III) may have resulted from cross-contamination via workers, flies, birds, air movement, or the environment. Alternatively, the inventors cannot rule out prior exposure, as these serotypes are frequently isolated from dairy cattle (3, 4, 12). A transdermal route of infection may account for some *Salmonella* recovered from the PLNs of cattle presented for harvest. The inventors shows a transdermal route of infection as the study IV challenge study. Multiple serotypes were used within the sample animal (i.e., Senftenberg and Montevideo or Senftenberg and Newport), and this route of challenge predictably resulted in positive PLNs. Moreover, the serogroups recovered from the PLNs that drain the challenge region (e.g., right foreleg to prescapular lymph node versus ventral abdomen to subiliac lymph node) matched in all but one instance. Similar to study I, a vaccine effect was observed for *Salmonella* Newport but not for *Salmonella* Montevideo.

Across all necropsy days, the relative magnitude of association between vaccine status and *Salmonella* Newport prevalence for studies I, III, and IV was 20.3, 39.4, and 50%, respectively. These data, in conjunction with the control prevalence, should inform the design and sample size calculations of future studies. While the ideal window in which to sample PLNs subsequent to challenge is not completely certain, the time periods described herein provide a reasonable estimate.

Example 3—

Recent studies have shown that *Salmonella* can routinely be recovered from peripheral lymph nodes of cattle and other animals. When *Salmonella* is harbored within lymph nodes it is protected from current interventions employed in abattoirs. Since these lymph nodes are often incorporated into ground meat, they may be a point of contamination within ground product. Using lymph nodes as a method to introduce *Salmonella* provides a model system for measuring and treating *Salmonella* distributed throughout ground meat during commercial production.

Illnesses associated with exposure to foodborne pathogens pose a significant economic burden on the United States each year (Scharff). Of the many known foodborne pathogens, *Salmonella enterica* is estimated to cause over 1 million illnesses annually (Scallan). It is widely accepted that cattle are associated with *Salmonella* the pathogen can persist on hides or in feces. As such, beef has been recognized as a vehicle for human exposure to *Salmonella* (Bacon; Fedorka-Cray; Fegan; Kunze; Loneragan).

Despite the use of effective post-harvest pathogen interventions within the abattoir, *Salmonella* is still present in retail ground beef. In a study of commercially produced ground beef, Bosilevac, recovered *Salmonella* from 4.2% of retail ground beef samples (n=4,136) collected from seven regions of the United States. *Salmonella* has been recovered from peripheral lymph nodes (PLN) of cattle at harvest. Because lymph nodes containing *Salmonella* are commonly present in lean and fat trimmings that are incorporated into ground beef, PLN are a likely a significant source of *Salmonella* contamination.

However, the majority of studies have only examined a select few nodes (e.g. subiliac and mesenteric lymph nodes) leaving a critical knowledge gap (Arthur; Brichta-Harhay; Gragg 2013a; Gragg 2013b; Haneklaus). The present inventors describe the prevalence and concentration of *Salmonella* in small PLN of cattle harvested in high- and medium-prevalence regions of the US, and evaluate and characterize the distribution of *Salmonella* in ground beef when the contamination arises from PLN.

Small PLN Sample Collection. A total of 1,270 PLN were collected from six anatomically distinct areas of the carcass (i.e. chuck plate fat side, chuck plate bone side, shoulder clod, loin, tenderloin, and popliteal) during fabrication from two separate commercial slaughter facilities (approximately 100 per each PLN type). Additionally, 50 subiliac lymph nodes were collected from each facility to facilitate some comparison of *Salmonella* prevalence estimates to historical data. Peripheral lymph nodes were not collected from the same carcass. Lymph nodes were placed in coolers with ice packs during transportation.

Lymph node samples were analyzed for the presence of *Salmonella* as previously described by Brichta-Harhay. Briefly, each node was aseptically trimmed from its surrounding adipose tissue and submerged in boiling water for 3 to 5 seconds for surface sterilization. Surface-sterilized lymph nodes were immediately placed in a sterile whirl-pack bag and weighed. Lymph nodes were then pulverized with a rubber mallet and enriched with 40 ml of tryptic soy broth (EMD Millipore, Billerica, Mass.). Culture and quantification procedures proceeded as described below and previously by Brichta-Harhay.

Grinding Study Processing. Peripheral lymph nodes were collected from steers challenged with *Salmonella* via transdermal inoculation as described by Edrington. Six PLN (i.e., pre-scapular, subiliac and popliteal lymph nodes collected from either side of the animal) were thoroughly mixed into 10 kilograms of 85/15 beef trim and ground using a ⅜-inch grinder plate to simulate a coarse grind. The ground product passed through a loafing attachment (Colosimo's Original, *Magna*, UT) and onto wax paper. The continuous ground beef loaf was portioned into approximately 100-gram samples and kept in chronological order. The residual ground beef left between the loafing attachment and the grinder plate, as well as, what was left in the auger was also collected and processed. Ground beef samples were individually placed into filtered sample bags and enriched with 400 ml of TSB. Culture and quantification procedures followed previously described methods Brichta-Harhay et al., (2012).

In a second study, PLN were collected from steers challenged with *Salmonella* via transdermal inoculation as described by Edrington et al., (2013). One PLN was ground with 10 kilograms of 85/15 beef trim and ground using a ⅜-inch grinder plate to simulate a coarse grind. First, 1 kg of trim was weighed and this was ground first. Then the lymph node and remaining 9 kg of trim were ground. The ground product passed through a loafing attachment and onto wax paper. The continuous ground beef loaf was portioned into approximately 100-gram samples and kept in chronological order. The residual ground beef left between the Colosimo attachment and the grinder plate, as well as, what was left in the auger was also collected and processed. Ground beef samples were individually placed into filtered sample bags and enriched with 400 ml of TSB and subjected to previously described culture and quantification procedures Brichta-Harhay et al., (2012).

For all studies, PLN and ground beef (GB) enrichments were plated onto dehydrated Enterobacteriaceae petrifilms in duplicate (PLN) or quadruplicate (GB) to determine the concentration of *Salmonella* present in each sample. For *Salmonella* confirmation, the incubated media films were pressed onto xylose lysine deoxycholate agar (Becton, Dickson, and Co., Sparks, Md.) and incubated at 37° C. for approximately 16 hours. Colonies displaying typical *Salmonella* morphology types were counted and reported as CFU/PLN or CFU/100 g GB, and CFU/gram of PLN or GB.

Peripheral lymph node and GB enrichments were incubated at 25° C. for 2 hours and then 42° C. for 12 hours. Immunomagnetic separation was performed on incubated sample enrichments using anti-*salmonella* DYNABEADS® (Invitrogen, Carlsbad, Calif.). Recovered beads (approximately 100 μl) were placed into 3 ml of Rappaport-Vassiliadis broth (Neogen, Lansing, Mich.) for secondary enrichment and incubated at 42° C. for 18-20 hours and then streaked to XLD and brilliant green sulfa agar (BGS). Typical colonies on XLD (black center) and BGS (bright pink) indicated *Salmonella*-positive samples.

For the small PLN study, the average weight of individual PLN collected was 0.5, 2.5, 4.1, 12.7, 13.6, and 14.4 grams among the shoulder clod, chuck plate, loin, tenderloin, subiliac, and popliteal lymph nodes, respectively. In all PLN samples collected from both facilities, *Salmonella* was recovered from 0, 3.9, 0.5, 0.5, 1, 3.5, 12.5 and 26% of chuck plate fat side (Plant 1 only), chuck plate bone side (Plant 1 only), chuck (Plant 2 only), shoulder clod, loin, tenderloin, subiliac and popliteal lymph nodes, respectively. The prevalence of *Salmonella* observed in subiliac lymph nodes (i.e. facility 1-13% and facility 2-12%) was similar to the reported findings of Gragg 2013a for fed cattle. Of the total PLN positive for *Salmonella* from both plants, 46% contained quantifiable levels. For positive PLN, *Salmonella* was found at 2.2, 1, 1.4, 0.9, and 3.2 $\log_{10}$ CFU/PLN among chuck plate bone side (Plant 1 only), chuck plate (Plant 2 only), tenderloin, subiliac, and popliteal lymph nodes, respectively.

Figure 5:
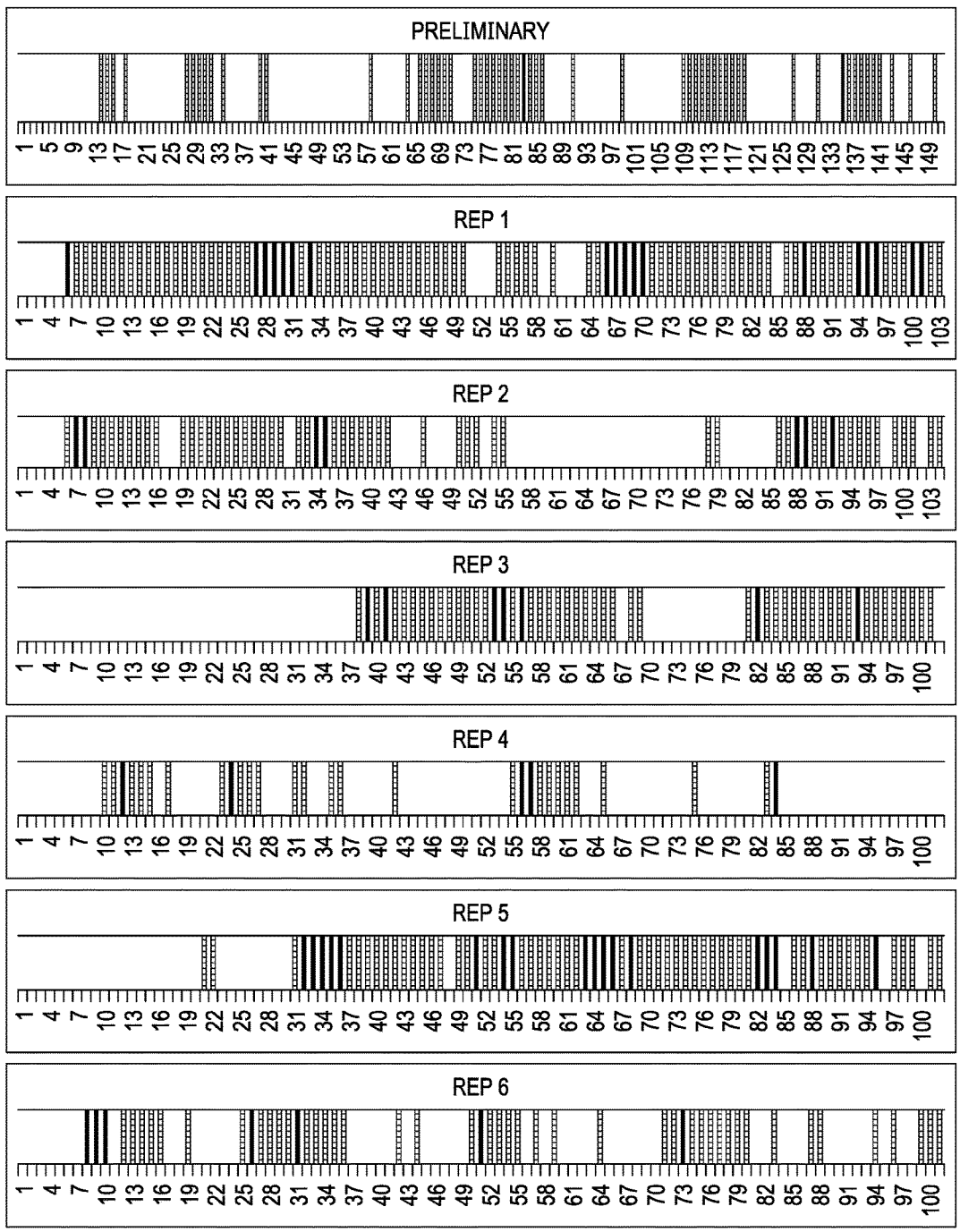

The distribution of qualitative and quantitative *Salmonella* recovery from course GB is presented in FIG. 5. The chart labeled REP 1 Preliminary was the first run through of the protocol. This rep was performed using 15 kg of trim and was an exploratory effort to fine-tune the model.

Another difference in this rep was that the lymph nodes were trimmed of all adipose tissue prior to grinding. For the remainder of the studies, 10 kg was used and the adipose tissue surrounding the lymph node was left to better reflect how lymph nodes are incorporated into trim for ground beef production. Because there were only two samples in the first (preliminary) rep that were quantifiable, the amount of trim used was reduced from 15 kg to 10 kg in order to try to increase the number of quantifiable samples.

The six reps of the initial grinding study (labeled REP 2-7) yielded very different results. The charts show the distribution of positive samples. The percentage of *Salmonella* positive samples in reps 2-7 were 87.4%, 56.7%, 50.9%, 28.4%, 68.6%, and 49.5%, respectively. Enumeration analysis of each sample resulted in a mean concentration of 2.28 $\log_{10}$ CFU per 100-g ground beef sample (GB) among quantifiable nodes.

Figure 6:
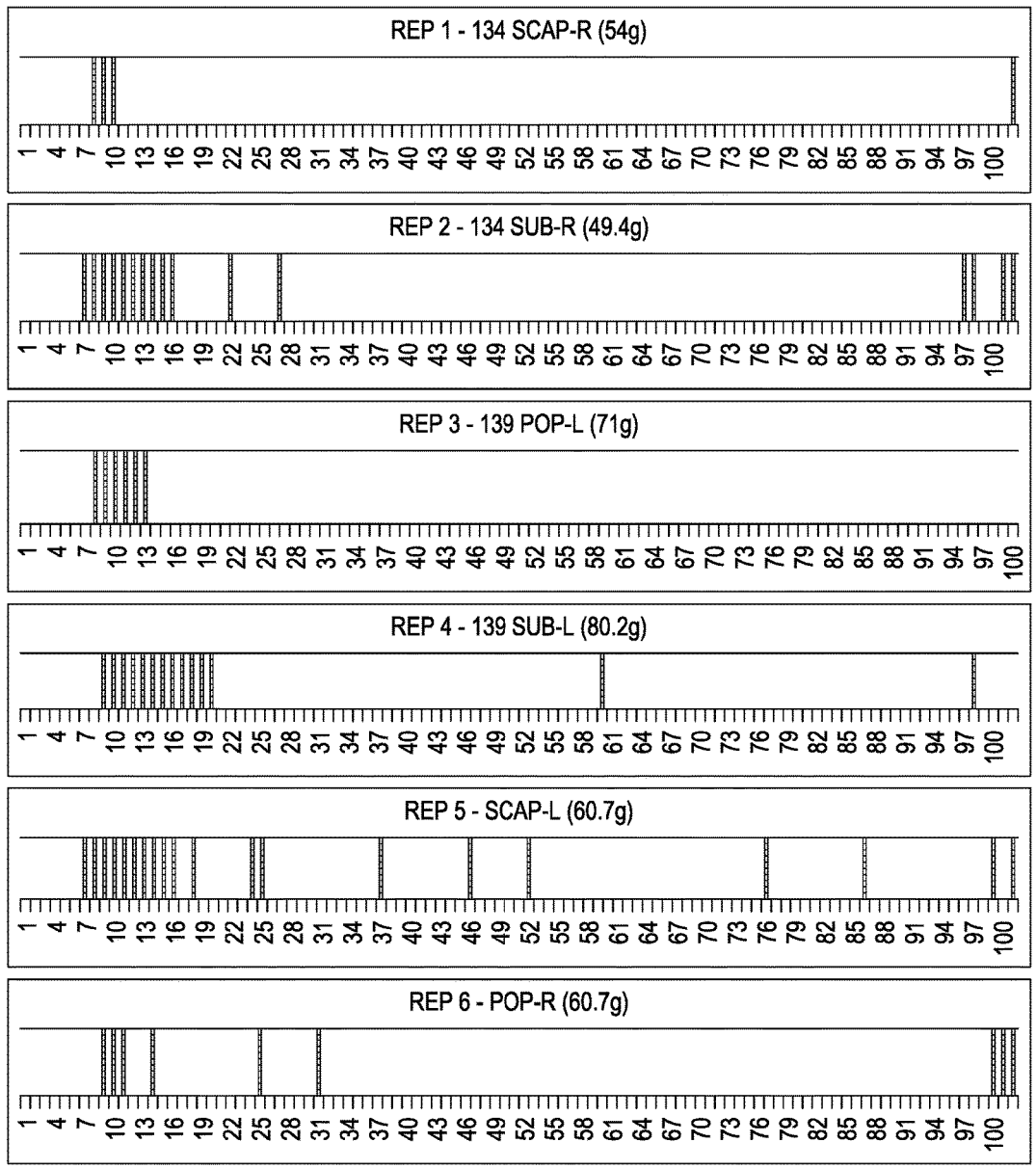
Figure 7:
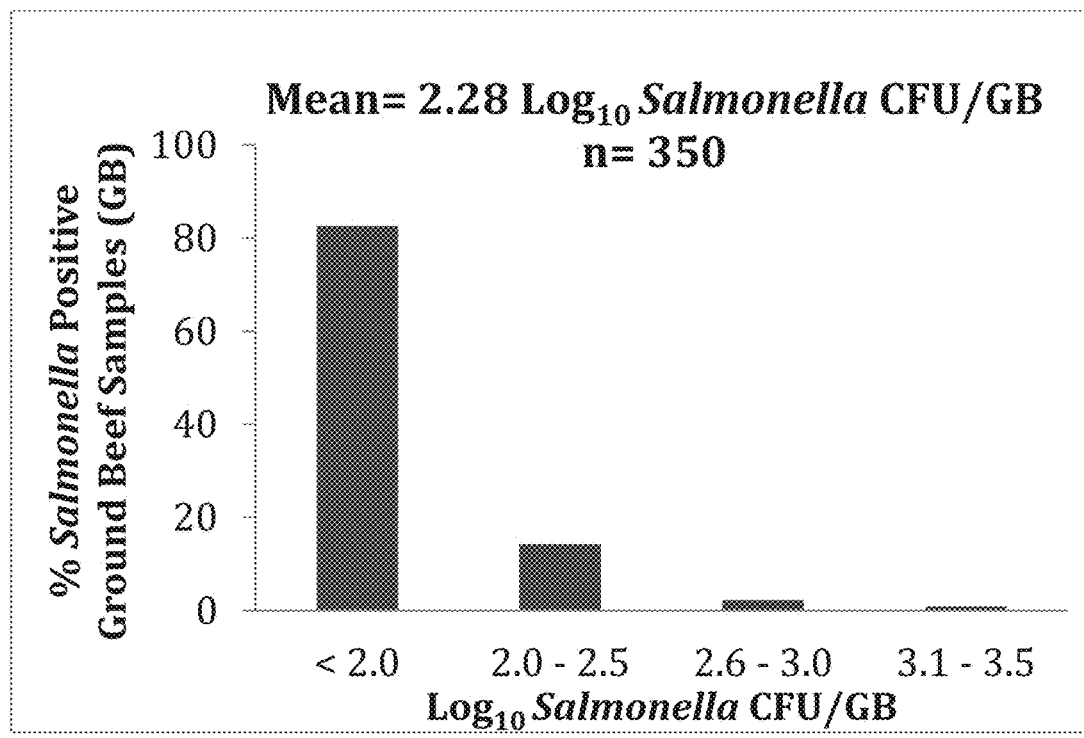

In reps 1-6 of the single node grinding study, the percentage of positive samples were 3.9%, 15.7%, 6.0%, 13.7%, 19.8%, and 8.8% respectively. There were no samples in the single node study that were enumerable. As part of the single node study ten lymph nodes were cultured to determine concentration of *Salmonella*. These lymph nodes were the remaining lymph nodes from each animal that weren't used in the grinding process. Each lymph node was divided into thirds in an effort to determine if the concentration is the same throughout the lymph node and provide insights into the *Salmonella* replication within PLN. *Salmonella* was not recovered from 3 of the lymph nodes, i.e., two popliteal from one animal and another popliteal from a different animal. The concentration of each part of the node varied to a limited degree, and not all parts of the each node were above the limit of quantification. The concentrations of each part as well as the whole lymph node are in presented in Tables 6A and 6B. FIG. 6 shows how the lymph node was divided into thirds. FIG. 7 shows the distribution of *Salmonella* concentration in ground beef samples.

TABLE 6A

Description of the peripheral lymph nodes generated using the transdermal route of infection and included in the grinding study.

| PLN | LN portion | Vessels | Color | +or– |
|---|---|---|---|---|
| 1 | 134 SUB---Ltop | | | – |
| 2 | 134 SUB---L | Efferent vessel | | + |
| 3 | 134 SUB---L | Afferent vessel | | + |
| 4 | 134 SCAP---L | | | + |
| 5 | 134 SCAP---L | Efferent vessel | | + |
| 6 | 134 SCAP---L | Afferent vessel | | + |
| 7 | 134 POP---R top | | | – |
| 8 | 134 POP---R | Efferent vessel | | – |
| 9 | 134 POP---R | Afferent vessel | | – |
| 10 | 134 POP---L top | Efferent vessel | | – |
| 11 | 134 POP---L | Afferent vessel | | – |
| 12 | 134 POP---L | | | – |
| 13 | 139 POP---R top | Efferent vessel | Normal | – |
| 14 | 139 POP---R | | Normal | – |
| 15 | 139 POP---R | | Normal | – |
| 16 | 139SUB---Rtop | | Normal | + |
| 17 | 139 SUB---R middle | Efferent & afferent vessel | Dark (blackish) | + |
| 18 | | | Dark (blackish) | + |
| 19 | 139SCAP---L | | Normal | + |
| 20 | 139 SCAP---L middle | Efferent vessel | ½ normal, ½ dark with blood spots | + |
| 21 | | | Dark, blood spots, hemal attached | + |
| 22 | 139 SCAP---R | Afferent vessel | Normal | + |
| 23 | 139 SCAP---R middle | Efferent vessel | ½ normal, ½ blood spots and dark | + |
| 24 | | Efferent vessel | Dark, blood spots Normal | + |
| 25 | POP---L top | | | – |
| 26 | POP---L middle | | ½ normal, ½ dark | – |
| 27 | POP---L bottom | Efferent & afferent vessel | Dark (blackish) | – |
| 28 | SCAP---R top | Afferent vessel | Blood spots | + |
| 29 | SCAP---R middle | Efferent & 5 afferent vessel | Blood spots | + |
| 30 | SCAP---R bottom | Afferent vessel | Blood spots, _lymph node with a hemal node attached | + |

TABLE 6B

Description of the peripheral lymph nodes generated using the transdermal route of infection and included in the grinding study.

| PLN | LN Portion | Log 10 CFU/LN | Log 10 CFU/g of LN |
|---|---|---|---|
| 2 | 134 SUB---L middle | 2.11 | 1.19 |
| 3 | 134 SUB---L bottom | 2.10 | 1.43 |
| 134 SUB---L | Whole node | 2.45 | 1.2 |
| 4 | 134SCAP---L top | 1.48 | 0.59 |
| 16 | 139SUB---Rtop | 1.05 | 0.17 |
| 17 | 139 SUB---R middle | 1.65 | 0.8 |
| 18 | 139 SUB---R bottom | 1.05 | 0.13 |
| 19 | 139 SCAP---L top | 2.17 | 1.07 |
| 139 SCAP---L | Whole node | 2.13 | 0.52 |
| 24 | 139 SCAP---R bottom | 1.05 | 0.08 |
| 139 SCAP---R | Whole node | 1.83 | 0.23 |
| 28 | SCAP---R top | 1.70 | 0.7 |
| 29 | SCAP---R middle | 1.95 | 0.94 |
| 30 | SCAP---R bottom | 1.48 | 0.48 |
| SCAP---R | Whole node | 2.56 | 1.09 |

Recent work on *Salmonella* within PLN of cattle has focused on establishing baseline prevalence data for a select few nodes (Arthur; Brichta-Harhay; Gragg; Haneklaus). Data from the present PLN study provides new and important findings on the burden of *Salmonella* in small PLN that are routinely exposed during carcass fabrication.

In this study, the inventors observed that *Salmonella* can be present within multiple small PLN of cattle, suggesting that *Salmonella* may be dispersed throughout the lymphatic system of infected cattle. In addition, collection of the subiliac and popliteal PLN provided a reasonable comparison to prior studies. The data described herein indicate that the burden of *Salmonella* in small PLN found widely throughout beef carcasses is low relative to that of large PLN (i.e., prescapular, subiliac and popliteal nodes). These data ought to inform risk assessment models and our understanding of the risk associated with small PLN, which appears to be low.

The improved understanding of the distribution of *Salmonella* within lymphatic tissue of harvest-ready cattle can inform beef processors of the risk associated with PLN during carcass fabrication. The data provided herein lead to a better understanding of the distribution—both qualitative and quantitative—of *Salmonella* in course ground product when the contamination arises from PLN. The distribution is highly clustered and clearly associated with entry of a PLN into the grind then once that tissue is pushed through the plate, *Salmonella* was no longer (or extremely rarely) recovered from the product. While these data provide valuable information for risk assessment efforts, they are somewhat limited in that a) the concentration of *Salmonella* in GB was relatively low in that in most instances it was not quantifiable and b) course ground beef is typically reground into a fine-ground product.

Because lymph nodes are often encased in fat, current interventions do not have an effect on *Salmonella* present within the lymph node. Inclusion of *Salmonella*-positive lymph nodes into ground beef leads to the development of practical interventions to reduce *Salmonella* contamination in trim and ground beef, including, apply an intervention prior to regrinding of course ground beef in to fine ground beef.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES—EXAMPLE 2

1. Arthur, T. M., D. M. Brichta-Harhay, J. M. Bosilevac, M. N. Guerini, N. Kalchayanand, J. E. Wells, S. D. Shackelford, T. L. Wheeler, and M. Koohmaraie. 2008. Prevalence and characterization of *Salmonella* in bovine lymph nodes potentially destined for use in ground beef. J. Food Prot. 71:1685-1688.
2. Brichta-Harhay, D. M., T. M. Arthur, J. M. Bosilevac, N. Kalchayanand, S. D. Shackleford, T. L. Wheeler, and M. Koohmar-aie. 2011. Diversity of multidrug-resistant *Salmonella enterica* strains associated with cattle at harvest in the United States. Appl. Environ. Microbiol. 77:1783-1796.
3. Brichta-Harhay, D. M., M. N. Guerini, T. M. Arthur, J. M. Bosilevac, N. Kalchayanand, S. D. Shackleford, T. L. Wheeler, and M. Koohmaraie. 2008. *Salmonella* and *Escherichia coli* O157:H7 contamination on hides and carcasses of cull cattle presented for slaughter in the United States: an evaluation of prevalence and bacterial loads by immunomagnetic separation and direct plating methods. Appl. Environ. Microbiol. 74:6289-6297.
4. Edrington, T. S., M. E. Hume, M. L. Looper, C. L. Schultz, A. C. Fitzgerald, T. R. Callaway, K. J. Genovese, K. M. Bischoff, J. L. McReynolds, R. C. Anderson, and D.

J. Nisbet. 2004. Variation in the faecal shedding of *Salmonella* and *E. coli* O157:H7 in lactating dairy cattle and examination of *Salmonella* genotypes using pulsed-field gel electrophoresis. Lett. Appl. Microbiol. 38:366-372.
5. Edrington, T. S., G. H. Loneragan, J. Hill, K. J. Genovese, D. M. Brichta-Harhay, R. L. Farrow, N. A. Krueger, T. R. Callaway, R. C. Anderson, and D. J. Nisbet. 2013. Development of challenge models to evaluate the efficacy of a vaccine to reduce carriage of *Salmonella* in peripheral lymph nodes of cattle. J. Food Prot. 76:1259-1263.
6. Haneklaus, A. N., K. B. Harris, D. B. Griffin, T. S. Edrington, L. M. Lucia, and J. W. Savell. 2012. *Salmonella* prevalence in bovine lymph nodes differs among feedyards. J. Food Prot. 75:1131-1133.
7. Koohmaraie, M., J. A. Scanga, M. J. De La Zerda, B. Koohmaraie, L. Topay, V. Beskhlebnaya, T. Mai, K. Greeson, and M. Samadpour. 2012. Tracking the sources of *Salmonella* in ground beef produced from nonfed cattle. J. Food Prot. 75:1464-1468.
8. Paulin, S. M., P. R. Watson, A. R. Benmore, M. P. Stevens, P. W. Jones, B. Villarreal-Ramos, and T. S. Wallis. 2002. Analysis of *Salmonella enterica* serotype-host specificity in calves: avirulence of S. enteric serotype *Gallinarum* correlates with bacterial dissemination from mesenteric lymph nodes and persistence in vivo. Infect. Immun. 70:6788-6797.
9. Pullinger, G. D., S. M. Paulin, B. Charleston, P. R. Watson, A. J. Bowen, F. Dziva, E. Morgan, B. Villarreal-Ramos, T. S. Wallis, and M. P. Stevens. 2007. Systemic translocation of *Salmonella enterica* serovar Dublin in cattle occurs predominantly via efferent lymphatics in a cell-free niche and requires type III secretion system 1 (T3SS-1) but not T3SS-2. Infect. Immun. 75:5191-5199.
10. Samuel, J. L., D. A. O'Boyle, W. J. Mathers, and A. J. Frost. 1979. Isolation of *Salmonella* from mesenteric lymph nodes of healthy cattle at slaughter. Res. Vet. Sci. 28:368-372.

REFERENCES—EXAMPLE 3

11. Arthur, T. M., D. M. Brichta-Harhay, J. M. Bosilevac, M. N. Guerini, N. Kalchayanand, J. E. Wells, S. D. Shackelford, T. L. Wheeler, and M. Koohmaraie. 2008. Prevalence and characterization of *Salmonella* in bovine lymph nodes potentially destined for use in ground beef. J. Food Prot. 71:1685-1688.
12. Dodd, C. C., D. G. Renter, D. U. Thomson, and T. G. Nagaraja. 2011. Evaluation of the effects of a commercially available *Salmonella* Newport siderophore receptor and porin protein vaccine on fecal shedding of *Salmonella* bacteria and health and performance of feedlot cattle. Am. J. Vet. Res. 2:239-247.
13. Edrington, T. S., T. R. Callaway, R. C. Anderson, and D. J. Nisbet. 2008. Prevalence of multidrug-resistant *Salmonella* on commercial dairies utilizing a single heifer raising facility. J. Food Prot. 71:27-34.
14. Edrington, T. S., B. H. Carter, T. H. Friend, G. R. Hagevoort, T. L. Poole, T. R. Callaway, R. C. Anderson, and D. J. Nisbet. 2009. Influence of sprinklers, used to alleviate heat stress, on faecal shedding of *E. coli* O157:H7 and *Salmonella* and antimicrobial susceptibility of *Salmonella* and *Enterococcus* in lactating dairy cattle. Lett. Appl. Microbiol. 48:738-743.
15. Edrington, T. S., G. H. Loneragan, J. Hill, K. J. Genovese, H. He, T. R. Callaway, R. C. Anderson, D. M. Brichta-Harhay, and D. J. Nisbet. 2013. Development of a transdermal *Salmonella* challenge model in calves. J. Food Prot. 76:1255-1258.
16. Farrow, R. L. 2012. Quantitative herd-level evaluation of a commercially available vaccine for control of *Salmonella* in dairy cattle. Ph.D. dissertation. Texas A&M University, College Station.
17. Haneklaus, A. N., K. B. Harris, D. B. Griffin, T. S. Edrington, L. M. Lucia, and J. W. Savell. 2012. *Salmonella* prevalence in bovine lymph nodes differs among feedyards. J. Food Prot. 75:1131-1133.
18. Heider, L. C., R. W. Meiring, A. E. Hoet, W. A. Gebreyes, J. A. Funk, and T. E. Wittum. 2008. Evaluation of vaccination with a commercial subunit vaccine on shedding of *Salmonella enterica* in subclinically infected dairy cows. J. Am. Vet. Med. Assoc. 233:466-469.
19. Hermesch, D. R., D. U. Thomson, G. H. Loneragan, D. R. Renter, and B. J. White. 2008. Effects of a commercially available vaccine against *Salmonella enterica* serotype Newport on milk production, somatic cell count, and shedding of *Salmonella* organisms in female dairy cattle with no clinical signs of *salmonellosis*. Am. J. Vet. Res. 9: 1229-1234.
20. Koohmaraie, M., J. A. Scanga, M. J. De La Zerda, B. Koohmaraie, L. Tapay, V. Beskhlebnaya, T. Mai, K. Greeson, and M. Samadpour. 2012. Tracking the sources of *Salmonella* in ground beef produced from nonfed cattle. J. Food Prot. 75:1464-1468.
21. Loneragan, G. H., D. U. Thomson, R. M. McCarthy, H. E. Webb, A. E. Daniels, T. S. Edrington, D. J. Nisbet, S. J. Trojan, S. C. Rankin, and M. M. Brashears. 2012. *Salmonella* diversity and burden in cows on and culled from dairy farms in the Texas high plains. Foodborne Pathog. Dis. 9:549-555.
22. U. S. Department of Agriculture, Food Safety and Inspection Service. 2010. Progress report on *Salmonella* testing of raw meat and poultry products, 1998-2010. Available at: www.fsis.usda.gov/PDF/*Salmonella* Progress Report 1998-2003.pdf. Accessed 10 Apr. 2013.

REFERENCES EXAMPLE 3

23. Arthur T M, Brichta-Harhay D M, Bosilevac J M, Guerini M N, Kalchayanand N, Wells J E, Shackelford S D, Wheeler T L and Koohmaraie M. Prevalence and Characterization of *Salmonella* in Bovine Lymph Nodes Potentially Destined for Use in Ground Beef. J Food Prot 2008; 71:1658-1688.
24. Bacon R T, Sofos J N, Belk K E, Hyatt D R and Smith G C. Prevalence and Antibiotic Susceptibility of *Salmonella* Isolated from Beef Animal Hides and Carcasses. J Food Prot 2002; 65:284-290.
25. Bosilevac J M, Guerini M N, Kalchayanand N and Koohmaraie M. Prevalence and characterization of salmonellae in commercial ground beef in the United States. Appl Environ Microbiol 2009; 75:1892-1900.
26. Brichta-Harhay D M, Arthur T M, Bosilevac J M, Kalchayanand N, Schmidt J W, Wang R, Shackelford S D, Loneragan G H and Wheeler T L. Microbiological analysis of bovine lymph nodes for the detection of *Salmonella enterica*. J Food Prot 2012; 75:854-858.
27. Edrington T S, Loneragan G H, Hill J, Genovese K J, He H, Callaway T R, Anderson R C, Brichta-Harhay D M and Nisbet D J. Development of a Transdermal *Salmonella* Challenge Model in Calves. J Food Prot 2013; 76:1255-1258.

28. Fedorka-Cray P J, Dargatz D A, Thomas L A and Gray J. Survey of *Salmonella* Serotypes in Feedlot Cattle. J Food Prot 1998; 61:525-530.
29. Fegan N, Vanderlinde P, Higgs G and Desmarchelier P. A Study of the Prevalence and Enumeration of *Salmonella enterica* in Cattle and on Carcasses during Processing. J Food Prot 2005; 68:1147-1153.
30. Gragg S E, Loneragan G H, Brashears M M, Arthur T M, Bosilevac J M, Kalchayanand N, Wang R, Schmidt J W, Brooks J C, Shackelford S D, Wheeler T L, Brown T R, Edrington T S and Brichta-Harhay D M. Cross-sectional study examining *Salmonella enterica* carriage in subiliac lymph nodes of cull and feedlot cattle at harvest. Foodborne Pathog Dis 2013a; 10:368-374.
31. Gragg S E, Loneragan G H, Nightingale K K, Brichta-Harhay D M, Ruiz H, Elder J R, Garcia L G, Miller M F, Echeverry A, Ramirez Porras R G and Brashears M M. Substantial within-animal diversity of *Salmonella* isolates from lymph nodes, feces, and hides of cattle at slaughter. Appl Environ Microbiol 2013b; 79:4744-4750.
32. Haneklaus A N, Harris K B, Griffin D B, Edrington T S, Lucia L M and Savell J W. *Salmonella* prevalence in bovine lymph nodes differs among feedyards. J Food Prot 2012; 75:1131-1133.
33. Kunze D J, Loneragan G H, Platt T M, Miller M F, Besser T E, Koohmaraie M, Stephens T and Brashears M M. *Salmonella enterica* burden in harvest-ready cattle populations from the southern high plains of the United States. Appl Environ Microbiol 2008; 74:345-351.
34. Loneragan G H, Thomson D U, McCarthy R M, Webb H E, Daniels A E, Edrington T S, Nisbet D J, Trojan S J, Rankin S C and Brashears M M. *Salmonella* diversity and burden in cows on and culled from dairy farms in the Texas High Plains. Foodborne Pathog Dis 2012; 9:549-555.
35. Scallan E, Hoekstra R M, Angulo F J, Tauxe R V, Widdowson M, Roy S L, Jones J L and Griffin P M. Foodborne Illness Acquired in the United States-Major Pathogens. Emerg Infect Dis 2011; 17:7-15.
36. Scharff R L. Economic Burden from Health Losses Due to Foodborne Illness in the United States. J Food Prot 2012; 75:123-131.

What is claimed is:

1. A method of introducing a pathogenic infection into one or more peripheral lymph nodes of an animal at one or more peripheral lymph node drainage areas for testing of meat, comprising:
inoculating at one or more peripheral lymph node drainage areas of the animal with a known amount of one or more known pathogens, wherein each of the one or more peripheral lymph node drainage areas comprise multiple lymph nodes;
harvesting the peripheral lymph nodes of the peripheral lymph node drainage areas at the site of inoculation from the animal;
separating the peripheral lymph nodes into individual lymph nodes;
determining if the individual lymph node is infected with the one or more known pathogens;
grinding meat or meat trimmings at the site of inoculation into ground meat; and
determining a ratio of the number of individual lymph nodes infected to a total number of lymph nodes and a weight of the meat or meat trimmings used to create the ground meat, wherein the infected ground meat can be used to test interventions against the known pathogen in a grinding process.

2. The method of claim 1, wherein the inoculation is selected from at least one of an intradermal, subdermal or transdermal inoculation.

3. The method of claim 1, wherein the pathogen is selected from at least one of *Salmonella, Listeria, Yersinia, Campylobacter, Shigella, E. coli, Francisella, Clostridum, Staphylococcus, Streptococcus*, or *Bacillus*, and strains thereof.

4. The method of claim 1, wherein the lymph node drainage areas comprise at least one of subiliac, popliteal, retropharangeal, superficial cervical, and axillary.

5. The method of claim 1, wherein the one or more known pathogens are selected from at least one of viral and protozoan pathogens.

6. The method of claim 1, wherein the animals comprise bovine, equine, ovine, porcine, or caprine.

7. The method of claim 1, further comprising the step of challenging the animal infected with the one or more pathogens at one or more sites with a therapeutic intervention to reduce or eliminate the one or more pathogens.

8. The method of claim 1, further comprising the step of titrating the amount of the known pathogen used during the inoculating step to obtain a pre-determined distribution of infected peripheral lymph nodes.

9. The method of claim 1, wherein the peripheral lymph nodes do not include gut associated lymph nodes.

10. The method of claim 1, wherein the meat prior to grinding is sterile.

11. A method of introducing an indicator bacteria into one or more peripheral lymph nodes of an animal to determine if a therapy, treatment or exposure eliminates or reduces the indicator bacteria comprising:
inoculating at one or more sites of the animal a known amount of the indicator bacteria, wherein the one or more inoculation sites comprise one or more peripheral lymph node drainage areas;
treating the animal with one or more therapies, treatments, or exposure at one or more time points;
harvesting the one or more peripheral lymph nodes from the animal that comprise the inoculated peripheral lymph nodes;
grinding the one or more peripheral lymph nodes with meat or meat trimmings known to be sterile into ground meat; and
determining if the one or more therapies, treatments, or exposure were effective to eliminate or reduce the indicator bacteria in the ground meat.

12. The method of claim 11, wherein the inoculation is selected from at least one of an intradermal, subdermal or transdermal inoculation.

13. The method of claim 11, wherein the indicator bacteria is selected from *Salmonella, Listeria, Yersinia, Campylobacter, Shigella, E. coli, Francisella, Clostridum, Staphylococcus, Streptococcus*, or *Bacillus*.

14. The method of claim 11, wherein the lymph node drainage areas comprise at least one of subiliac, popliteal, retropharangeal, superficial cervical, and axillary.

15. The method of claim 11, wherein the animals comprise bovine, equine, ovine, porcine, or caprine.

16. The method of claim 11, further comprising the step of titrating the amount of the indicator bacteria used during the inoculating step to obtain a pre-determined distribution of infected peripheral lymph nodes.

17. The method of claim 11, wherein the peripheral lymph nodes do not include gut associated lymph nodes.

18. A method of testing a compound for elimination of bacterial infections within the lymph nodes of an animal comprising:
- inoculating at one or more sites on the animal with a known amount of said bacteria, wherein the one or more inoculation sites comprise peripheral lymph node drainage areas;
- treating the animal with one or more compounds at one or more time points;
- harvesting from the animal the inoculated peripheral lymph nodes;
- grinding the harvested peripheral lymph nodes with meat or meat trimmings that are sterile into ground meat; and
- determining if the one or more compounds were effective to eliminate or reduce the bacteria.

19. The method of claim 18, wherein the inoculation is selected from at least one of an subdermal or transdermal inoculation.

20. The method of claim 18, wherein the bacteria is selected from *Salmonella, Listeria, Yersinia, Campylobacter, Shigella, E. coli, Francisella, Clostridum, Staphylococcus, Streptococcus*, or *Bacillus*.

21. The method of claim 18, wherein the lymph node drainage areas comprise at least one of subiliac, popliteal, retropharangeal, superficial cervical, and axillary.

22. The method of claim 18, wherein the animals comprise bovine, equine, ovine, porcine, or caprine.

23. The method of claim 18, wherein the bacteria is selected from *Salmonella* Newport and Montevideo.

* * * * *